(12) United States Patent
Kojima et al.

(10) Patent No.: US 7,803,553 B2
(45) Date of Patent: Sep. 28, 2010

(54) METHODS OF USE OF ANTIBODIES WHICH RECOGNIZE A PROTEASE CLEAVAGE SITE OF AN LAP FRAGMENT OF TGF-β

(75) Inventors: Soichi Kojima, Ibaraki (JP); Naoshi Dohmae, Saitama (JP); Wakako Kondo, Niigata (JP)

(73) Assignee: RIKEN, Saitama (JP)

( * ) Notice: Subject to any disclaimer, the term of this patent is extended or adjusted under 35 U.S.C. 154(b) by 790 days.

(21) Appl. No.: 10/570,606

(22) PCT Filed: Sep. 3, 2004

(86) PCT No.: PCT/JP2004/013189

§ 371 (c)(1),
(2), (4) Date: Oct. 24, 2006

(87) PCT Pub. No.: WO2005/023870

PCT Pub. Date: Mar. 17, 2005

(65) Prior Publication Data

US 2008/0038748 A1 Feb. 14, 2008

(30) Foreign Application Priority Data

Sep. 4, 2003 (JP) ............................... 2003-313014

(51) Int. Cl.
*G01N 33/53* (2006.01)
(52) U.S. Cl. ...................................... 435/7.1
(58) Field of Classification Search ....................... None
See application file for complete search history.

(56) References Cited

U.S. PATENT DOCUMENTS

2005/0164909 A1* 7/2005 Marsh et al. .................. 514/2
2008/0206219 A1* 8/2008 Coussens et al. ........... 424/94.4

OTHER PUBLICATIONS

Khalil N., Microbes and Infection, 1999, 1: 1255-1263.*
U.S. Appl. No. 12/044,463 to S. Kojima et al., entitled INHIBITOR of TGFβ Activation Reaction, filed Mar. 7, 2008.
Derynck R. et al., "Human transforming growth factor-β complementary DNA sequence and expression in normal and transformed cells" Nature, vol. 316, pp. 701-705, 1985.
Kondo et al., "Molecular Mechanism and Regulation of Latent TGF-β Activation", Journal of the Japanese Society on Thrombosis and Hemostasis, vol. 14, No. 3, pp. 210-219, 2003.
Bickerstaff AA., et al., "Mechanism of Graft Acceptance: Evidence That Plasminogen Activator Controls Donor-Reactive Delayed-Type Hypersensitivity Responses in Cardiac Allograft Acceptor Mice", Journal of Immunology, vol. 164, pp. 5132-5139, 2000.
Yehualaeshet T. et al., "Activation of Rat Alveolar Macrophage-Derived Latent Transforming Growth Factor β-1 by Plasmin requires Interation with Thrombispondin-1 and its Cell Surface Receptor, CD36", American Journal of Pathology, vol. 155, No. 3, pp. 841-851, 1999.

Okuno et al., "Prevention of Rat Hepatic Fibrosis by the Protease Inhibitor, Camostat Mesilate, via Reduced Generation of Active TGF-β", Gastroenterology, vol. 120, pp. 1784-1800, 2001.
Akita et al., "Impairted Liver Regeneration in Mice by Lipopolysaccharide Via TNF-α/Kallikrein-Mediated Activation of Latent TGF-β",Gastroenterology, vol. 123, pp. 352-364, 2002.
Annes et al., "Making sense of latent TGF β activation", Journal of Cell Science, vol. 116, pp. 217-224, 2003.
Bissell et al., "Cell-specific Expression of Transforming Growth Factor- βin Rat Liver", Journal of Clinical Investigation, vol. 96, pp. 447-455, 1995.
English Language Abstract of JP 2003-252792.
G. Kohler et al., "Continuous cultures of fused cells secreting antibody of predefined specificity", Nature, vol. 256, pp. 495-497, 1975.
U. K. Laemmli, "Cleavage of Structural Proteins during the Assembly of the Head of Bacteriophage T4", Nature vol. 227, pp. 680-685, 1970.
Higgins G.M. et al., "Experimental Pathology of the Liver" Arch Pathology, vol. 12, pp. 186-202, 1931.
C.G. Knight et al., "A Novel coumarin-labelled peptide for sensitive continuous assays of the matrix metalloproteinases", FEBS Letters, vol. 296, pp. 263-266, 1992.
Harlow and Lane, Immunassays, In Antibodies-A Laboratory Manual, Cold Spring Harbour Laboratory, New York, pp. 553-612, 1988.
International Preliminary Report on Patentability for PCT/JP2004/013189, mailed Jul. 6, 2006.
H. Kang et al., "Semaphorin 7A Plays a Critical Role in TGF-$β_1$ - Induced Pulmonary Fibrosis," The Journal of Experimental Medicine, vol. 204, No. 5, pp. 1083-1093, 2007.
M. Ruiz-Ortega et al., "TGF-β Signaling in Vascular Fibrosis," Cardiovascular Research, vol. 74, pp. 196-206, 2007.
D. Grainger, "TGF-β and Atherosclerosis in Man," Cardiovascular Research, vol. 74, pp. 213-222, 2007.
J. Varga et al., "Transforming Growth Factor β as a Therapeutic Target in Systemic Sclerosis," Nature Reviews Rheumatology, vol. 5, pp. 200-206, 2009.
A. M. El Nahas et al., "Chronic Kidney Disease: the Global Challenge," Lancet, vol. 365, pp. 331-340, 2005.

* cited by examiner

*Primary Examiner*—Ilia Ouspenski
(74) *Attorney, Agent, or Firm*—Greenblum & Bernstein, P.L.C.

(57) ABSTRACT

It is an object of the present invention to provide antibodies capable of detecting an active TGF-β generation reaction that is specific to pathogenesis, tissues, or isoforms. The present invention provides antibodies against an LAP fragment (or latent TGF-β) generated as a result of generation of active form of human TGF-β1, human TGOF-β2 and human TGF-β3. The antibodies are able to specifically recognize respective cutting edges within protease cleavage sites existing in the region from the amino acid residue glycine at position 51 to the amino acid residue arginine at position 110 of human TGF-β1, and corresponding regions of human TGF-β2 and human TGF-β3.

18 Claims, 12 Drawing Sheets

Tissue or isoform-specific TGF-β activation reaction

SEQUENCE LISTING

```
<160> NUMBER OF SEQ ID NOS: 5

<210> SEQ ID NO 1
<211> LENGTH: 391
<212> TYPE: PRT
<213> ORGANISM: Homo sapiens

<400> SEQUENCE: 1

Met Pro Pro Ser Gly Leu Arg Leu Leu Pro Leu Leu Leu Pro Leu Leu
 1               5                  10                  15

Trp Leu Leu Val Leu Thr Pro Gly Pro Pro Ala Ala Gly Leu Ser Thr
             20                  25                  30

Cys Lys Thr Ile Asp Met Glu Leu Val Lys Arg Lys Arg Ile Glu Ala
         35                  40                  45

Ile Arg Gly Gln Ile Leu Ser Lys Leu Arg Leu Ala Ser Pro Pro Ser
     50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125
```

```
His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Arg
145                 150                 155                 160

Leu Lys Leu Lys Val Glu Gln His Val Glu Leu Tyr Gln Lys Tyr Ser
                165                 170                 175

Asn Asn Ser Trp Arg Tyr Leu Ser Asn Arg Leu Leu Ala Pro Ser Asp
            180                 185                 190

Ser Pro Glu Trp Leu Ser Phe Asp Val Thr Gly Val Val Arg Gln Trp
        195                 200                 205

Leu Ser Arg Gly Gly Glu Ile Glu Gly Phe Arg Leu Ser Ala His Cys
    210                 215                 220

Ser Cys Asp Ser Arg Asp Asn Thr Leu Gln Val Asp Ile Asn Gly Phe
225                 230                 235                 240

Thr Thr Gly Arg Arg Gly Asp Leu Ala Thr Ile His Gly Met Asn Arg
                245                 250                 255

Pro Phe Leu Leu Leu Met Ala Thr Pro Leu Glu Arg Ala Gln His Leu
            260                 265                 270

Gln Ser Ser Arg His Arg Arg Ala Leu Asp Thr Asn Tyr Cys Phe Ser
        275                 280                 285

Ser Thr Glu Lys Asn Cys Cys Val Arg Gln Leu Tyr Ile Asp Phe Arg
    290                 295                 300

Lys Asp Leu Gly Trp Lys Trp Ile His Glu Pro Lys Gly Tyr His Ala
305                 310                 315                 320

Asn Phe Cys Leu Gly Pro Cys Pro Tyr Ile Trp Ser Leu Asp Thr Gln
                325                 330                 335

Tyr Ser Lys Val Leu Ala Leu Tyr Asn Gln His Asn Pro Gly Ala Ser
            340                 345                 350

Ala Ala Pro Cys Cys Val Pro Gln Ala Leu Glu Pro Leu Pro Ile Val
        355                 360                 365

Tyr Tyr Val Gly Arg Lys Pro Lys Val Glu Gln Leu Ser Asn Met Ile
    370                 375                 380

Val Arg Ser Cys Lys Cys Ser
385                 390

<210> SEQ ID NO 2
<211> LENGTH: 2745
<212> TYPE: DNA
<213> ORGANISM: Homo sapiens

<400> SEQUENCE: 2
acctccctcc gcggagcagc cagacagcga gggccccggc cggggcaggg gggacgccc         60 cgtccgggc accccccccg gctctgagcc gcccgcgggg ccggcctcgg cccggagcgg        120
aggaaggagt cgccgaggag cagcctgagg ccccagagtc tgagacgagc cgccgccgcc       180
cccgccactg cggggaggag ggggaggagg agcgggagga gggacgagct ggtcgggaga       240
agaggaaaaa aacttttgag acttttccgt tgccgctggg agccggaggc gcggggacct       300
cttggcgcga cgctgccccg cgaggaggca ggacttgggg accccagacc gcctcccttt       360
gccgccgggg acgcttgctc cctccctgcc cctacacgg cgtccctcag gcgcccccat        420
tccggaccag ccctcgggag tcgccgaccc ggcctcccgc aaagactttt ccccagacct      480
cgggcgcacc ccctgcacgc cgccttcatc ccggcctgt ctcctgagcc cccgcgcatc       540 ctagacccctt tctcctccag gagacggatc tctctccgac ctgccacaga tccctattc     600
```

| | |
|---|---|
| aagaccaccc accttctggt accagatcgc gcccatctag gttatttccg tgggatactg | 660 |
| agacaccccc ggtccaagcc tcccctccac cactgcgccc ttctccctga ggagcctcag | 720 |
| cttcccctcg aggccctcct accttttgcc gggagacccc cagcccctgc aggggcgggg | 780 |
| cctcccacc acaccagccc tgttcgcgct ctcggcagtg ccgggggcg ccgcctcccc | 840 |
| catgccgccc tccgggctgc ggctgctgcc gctgctgcta ccgctgctgt ggctactggt | 900 |
| gctgacgcct ggcccgccgg ccgcgggact atccacctgc aagactatcg acatggagct | 960 |
| ggtgaagcgg aagcgcatcg aggccatccg cggccagatc ctgtccaagc tgcggctcgc | 1020 |
| cagcccccg agccaggggg aggtgccgcc cggcccgctg cccgaggccg tgctcgccct | 1080 |
| gtacaacagc cccgcgacc gggtggccgg ggagagtgca gaaccggagc ccgagcctga | 1140 |
| ggccgactac tacgccaagg aggtcacccg cgtgctaatg gtggaaaccc acaacgaaat | 1200 |
| ctatgacaag ttcaagcaga gtacacacag catatatatg ttcttcaaca catcagagct | 1260 |
| ccgagaagcg gtacctgaac ccgtgttgct ctcccgggca gagctgcgtc tgctgaggag | 1320 |
| gctcaagtta aaagtggagc agcacgtgga gctgtaccag aaatacagca acaattcctg | 1380 |
| gcgatacctc agcaaccggc tgctggcacc cagcgactcg ccagagtggt tatcttttga | 1440 |
| tgtcaccgga gttgtgcggc agtggttgag ccgtggaggg gaaattgagg gctttcgcct | 1500 |
| tagcgccac tgctcctgtg acagcaggga taacacactg caagtggaca tcaacgggtt | 1560 |
| cactaccggc cgccgaggtg acctggccac cattcatggc atgaaccggc ctttcctgct | 1620 |
| tctcatggcc accccgctgg agagggccca gcatctgcaa agctcccggc accgccgagc | 1680 |
| cctggacacc aactattgct tcagctccac ggagaagaac tgctgcgtgc ggcagctgta | 1740 |
| cattgacttc cgcaaggacc tcggctggaa gtggatccac gagcccaagg gctaccatgc | 1800 |
| caacttctgc ctcgggccct gccctacat ttggagcctg gacacgcagt acagcaaggt | 1860 |
| cctggccctg tacaaccagc ataacccggg cgcctcggcg cgccgtgct gcgtgccgca | 1920 |
| ggcgctggag ccgctgccca tcgtgtacta cgtgggccgc aagcccaagg tggagcagct | 1980 |
| gtccaacatg atcgtgcgct cctgcaagtg cagctgaggt cccgccccgc ccgccccgc | 2040 |
| cccggcaggc ccggccccac cccgccccgc cccgctgcc ttgcccatgg gggctgtatt | 2100 |
| taaggacacc gtgccccaag cccacctggg gccccattaa agatggagag aggactgcgg | 2160 |
| atctctgtgt cattgggcgc ctgcctgggg tctccatccc tgacgttccc ccactcccac | 2220 |
| tccctctctc tccctctctg cctcctcctg cctgtctgca ctattccttt gcccggcatc | 2280 |
| aaggcacagg ggaccagtgg ggaacactac tgtagttaga tctatttatt gagcaccttg | 2340 |
| ggcactgttg aagtgcctta cattaatgaa ctcattcagt caccatagca acactctgag | 2400 |
| atggcaggga ctctgataac acccatttta aaggttgagg aaacaagccc agagaggtta | 2460 |
| agggaggagt tcctgcccac caggaacctg ctttagtggg ggatagtgaa gaagacaata | 2520 |
| aaagatagta gttcaggcca ggcggggtgc tcacgcctgt aatcctagca cttttgggag | 2580 |
| gcagagatgg gaggatactt gaatccaggc atttgagacc agcctgggta acatagtgag | 2640 |
| accctatctc tacaaaacac ttttaaaaaa tgtacacctg tggtcccagc tactctggag | 2700 |
| gctaaggtgg gaggatcact tgatcctggg aggtcaaggc tgcag | 2745 |

<210> SEQ ID NO 3
<211> LENGTH: 65
<212> TYPE: PRT
<213> ORGANISM: Homo sapiens

<400> SEQUENCE: 3

-continued

```
Arg Gly Gln Ile Leu Ser Lys Leu Lys Leu Thr Ser Pro Pro Glu Asp
 1               5                  10                  15

Tyr Pro Glu Pro Glu Val Pro Pro Glu Val Ile Ser Ile Tyr Asn
            20                  25                  30

Ser Thr Arg Asp Leu Leu Gln Glu Lys Ala Ser Arg Arg Ala Ala Ala
            35                  40                  45

Cys Glu Arg Glu Arg Ser Asp Glu Glu Tyr Tyr Ala Lys Glu Val Tyr
 50                  55                  60

Lys
 65

<210> SEQ ID NO 4
<211> LENGTH: 64
<212> TYPE: PRT
<213> ORGANISM: Homo sapiens

<400> SEQUENCE: 4

Arg Gly Gln Ile Leu Ser Lys Leu Arg Leu Thr Ser Pro Pro Glu Pro
 1               5                  10                  15

Thr Val Met Thr His Val Pro Tyr Gln Val Leu Ala Leu Tyr Asn Ser
            20                  25                  30

Thr Arg Glu Leu Leu Glu Glu His Gly Glu Arg Lys Glu Glu Gly Cys
            35                  40                  45

Thr Gln Glu Asn Thr Glu Ser Glu Tyr Tyr Ala Lys Glu Ile His Lys
 50                  55                  60

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: A2pr(Dnp)

<400> SEQUENCE: 5

Pro Leu Gly Leu Xaa Ala Arg
 1               5
```

METHODS OF USE OF ANTIBODIES WHICH RECOGNIZE A PROTEASE CLEAVAGE SITE OF AN LAP FRAGMENT OF TGF-β

TECHNICAL FIELD

The present invention relates to the antibodies that recognize cutting edge within the TGF-β activation controlling region, and a use thereof.

BACKGROUND ART

Transforming growth factor (TGF)-β strongly promotes generation of the extracellular matrices of mesenchymal cells, and at the same time, it suppresses the growth of epithelial cells, so as to promote pathogenesis of sclerotic diseases such as hepatic fibrosis/cirrhosis, atherosclerosis, lung fibrosis, scleroderma, or renal failure. On the other hand, TGF-β suppresses the action of immune cells. TGF-β is a multifunctional cytokine acting as a homodimer with a molecular weight of 25 kD, which exhibits various biological activities. As a result of studies using a combination of the neutralizing antibody to TGF-β and animal models, it has been revealed that sclerotic diseases can be prevented or cured by suppressing the action of TGF-β. For example, Okuno et al. Gastroenterology 120: 1784-1800, 2001 describes the prevention or treatment of hepatic fibrosis/cirrhosis by suppressing a TGF-β activation reaction using a protease inhibitor. Moreover, Akita et al. Gastroenterology 123: 352-364, 2002 describes promotion of liver regeneration by suppressing a TGF-β activation reaction using an antibody to protease. In addition, there are several review articles on TGF-β activation reaction, such as Kondo et al., Journal of the Japanese Society on Thrombosis and Hemostasis, 14 (3): 210-219, 2003, and Annes et al. J Cell Sci 116: 217-224, 2003.

On the other hand, TGF-β also plays an important role to maintain our health. For example, TGF-β suppresses excessive generation of proteases in lung and prevents lung tissue from destruction leading to emphysema. It also suppresses the growth of cancer cells, Furthermore, TGF-β has three isoforms, β1, β2 and β3, which exhibit almost the same biological activities. Thus, it has been desired to develop the technique, useful for treatment of diseases and prediction of prognosis, which detect and suppress pathogenesis-, tissues- or isoforms-specific TGF-β generation reactions, so as to block aberrant generation of a certain TGF-β isoform during the progression of pathogenesis. However, it has been difficult to detect such specific TGF-β generation reactions using the hitherto reported techniques.

Although there are established techniques to determine the isoform types of generated TGF-β in a certain lesion during pathogenesis process in animal models or patients utilizing antibodies (manufactured by R & D, or Sant Cruz) or gene probes (Bissell et al. J Clin Invest 96: 447-455, 1995) specific to each TGF-β isoform, since pathogenesis-, tissue-, or isoform-specific TGF-β generation reaction can not be detected by these techniques, these techniques have not allowed to develop a specific method for therapy or prevention of the diseases.

DISCLOSURE OF THE INVENTION

TGF-β is activated depending upon pathologic conditions, tissues, or isoform. As TGF-β is cleaved and activated with proteases such as plasmin and plasma kallikrein in the liver, it has been demonstrated that inhibition of the activity of these proteases with a low-molecular-weight synthetic protease inhibitor (Ono, FOY) or with an antibody (Japanese Patent Application No. 2002-057253) prevents pathogenesis of the diseases in animal models. However, there is no established technique to determine whether the same thing happens also in humans, or what type of activation reaction takes place in human.

An object of the present invention is to provide antibodies capable of detecting an active TGF-β generation reaction specific to pathogenesis, tissues, or isoforms. Another object of the present invention is to provide a method for detecting a TGF-β generation reaction using the above antibodies. A further object of the present invention is to develop a specific diagnostic method using the above antibody against TGF-β-associated diseases including, as typical examples, sclerotic diseases such as hepatic fibrosis/cirrhosis, atherosclerosis, lung fibrosis, scleroderma, or renal failure.

In the present invention, the inventors have resolved the aforementioned objects by focusing on the fact that TGF-β is activated in a pathogenesis-, tissue-, or isoform-specific manner, and by providing antibodies specific to a fragment generated as a result of active TGF-β generation reactions.

That is to say, the present invention provides antibodies against LAP fragments of human TGF-β, capable of specifically recognizing the cutting edge of a protease cleavage site within human TGF-β.

Preferably, the present invention provides antibodies against LAP fragments of human TGF-β1, human TGF-β2 and human TGF-β3, capable of specifically recognizing the cutting edge of a protease cleavage site located in the region from the amino acid residue glycine at position 51 to the amino acid residue arginine at position 110 of human TGF-β1 as well as the corresponding regions of human TGF-β2 and human TGF-β3.

The antibodies of the present invention may be either polyclonal antibodies or monoclonal antibodies.

Specific examples of these antibodies in the present invention may include the following antibodies:

an antibody specifically recognizing the cutting edge ending at the leucine residue at position 59, wherein a protease cleavage site is between the arginine residue at position 58 and the leucine residue at position 59;

an antibody specifically recognizing the cutting edge ending at the arginine residue at position 58, wherein a protease cleavage site is between the arginine residue at position 58 and the leucine residue at position 59;

an antibody specifically recognizing the cutting edge ending at the leucine residue at position 57, wherein a protease cleavage site is between the lysine residue at position 56 and the leucine residue at position 57;

an antibody specifically recognizing the cutting edge ending at the lysine residue at position 56, wherein a protease cleavage site is between the lysine residue at position 56 and the leucine residue at position 57;

an antibody specifically recognizing the cutting edge ending at the leucine residue at position 80, wherein a protease cleavage site is between the alanine residue at position 79 and the leucine residue at position 80;

an antibody specifically recognizing the cutting edge ending at the alanine residue at position 79, wherein a protease cleavage site is between the alanine residue at position 79 and the leucine residue at position 80;

an antibody specifically recognizing the cutting edge ending at the aspartic acid residue at position 86, wherein a protease cleavage site is between the arginine residue at position 85 and the aspartic acid residue at position 86;

an antibody specifically recognizing the cutting edge ending at the arginine residue at position 85, wherein a protease cleavage site is between the arginine residue at position 85 and the aspartic acid residue at position 86;

an antibody specifically recognizing the cutting edge ending at the glutamic acid residue at position 107, wherein a protease cleavage site is between the lysine residue at position 106 and the glutamic acid residue at position 107;

an antibody specifically recognizing the cutting edge ending at the lysine residue at position 106, wherein a protease cleavage site is between the lysine residue at position 106 and the glutamic acid residue at position 107;

an antibody specifically recognizing the cutting edge ending at the valine residue at position 77, wherein a protease cleavage site is between the alanine residue at position 76 and the valine residue at position 77; and an antibody specifically recognizing the cutting edge ending at the alanine residue at position 76, wherein a protease cleavage site is between the alanine residue at position 76 and the valine residue at position 77.

In another aspect, the present invention provides a diagnostic agent, which comprises the above-described antibodies of the present invention, for TGF-β-associated diseases including sclerotic diseases as typical examples.

In a further aspect, the present invention provides a method for detecting or measuring the activation reactions of human TGF-β1, human TGF-β2, and human TGF-β3 existing in samples or tissues, using the above-described antibodies of the present invention. In a further aspect, the present invention provides a method for diagnosing sclerotic diseases, which comprises detecting or measuring the activation reactions of human TGF-β1, human TGFβ2, and human TGF-β3 existing in samples or tissues, using the above-described antibodies of the present invention.

A: Factors enhancing the synthesis and/or secretion of TGF-β

Figure 2:
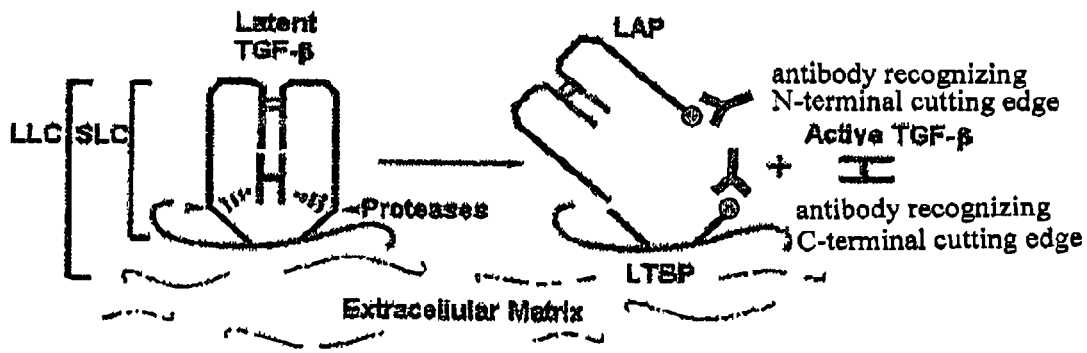

TGF-β, vitamin A, antiestrogen, bleomycin, dexamethasone, virus infection, activation of lymphocytes, bone fracture, hepatic fibrosis, myocardial infarction, hepatic injury B: factors releasing TGF-β from extracellular matrix
Elastase, zymase, plasmin, thrombin C: Factors causing activation of TGF-β
Acid, alkali, heat, denaturant, reactive oxygen species (ROS), endoglycosidase, thrombospondin, serine protease, integrin, matrix metalloprotease D: Factors causing TGF-β activation in cells
Mixed culture, vitamin A, vitamin D, antiestrogen, bleomycin, dexamethasone, lipopolysaccharide, IgG, interferon, carcinogenesis E: Factors enhancing expression of TGF-β receptor
Vitamin A, hepatic fibrosis F: Factors suppressing expression of TGP-β receptor
Carcinogenesis, extracellular matrix FIG. 2 shows tissue or isoform-specific TGF-β activation reaction. An LAP fragment is recognized by a newly produced antibody that recognizes the C-terminal cutting edge of a plasma kallikrein cleavage site. It is predicted that many LAP fragments remain in extracellular matrices via LTBP.

Figure 3:
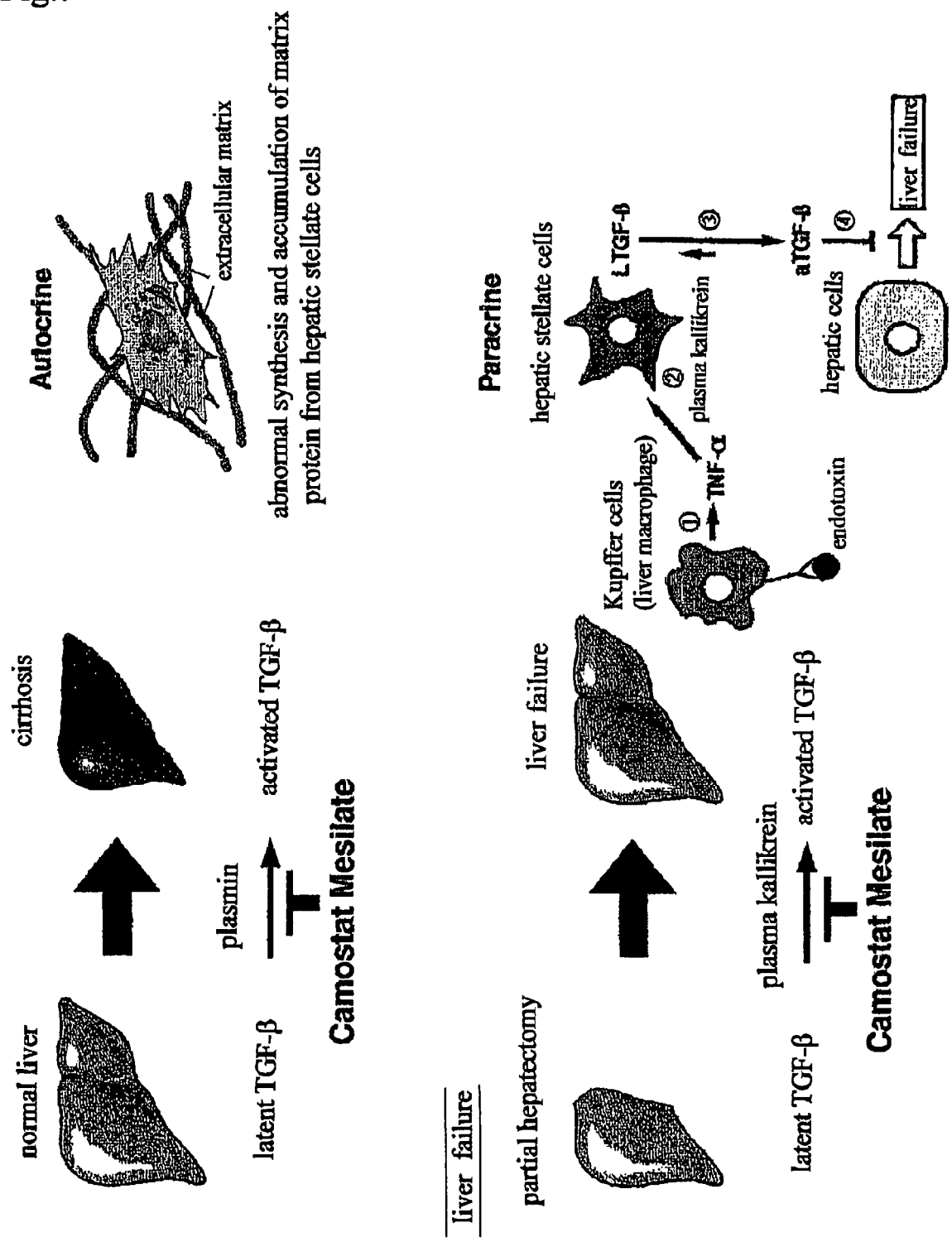

FIG. 3 shows proteolytic activation of TGF-β during pathogenesis of sclerotic diseases. TGF-β is activated by proteases specific to individual pathologic conditions, not only in hepatic cirrhosis and impaired liver regeneration, but also in other sclerotic diseases including atherosclerosis, lung fibrosis, scleroderma, and renal failure.

Figure 4:
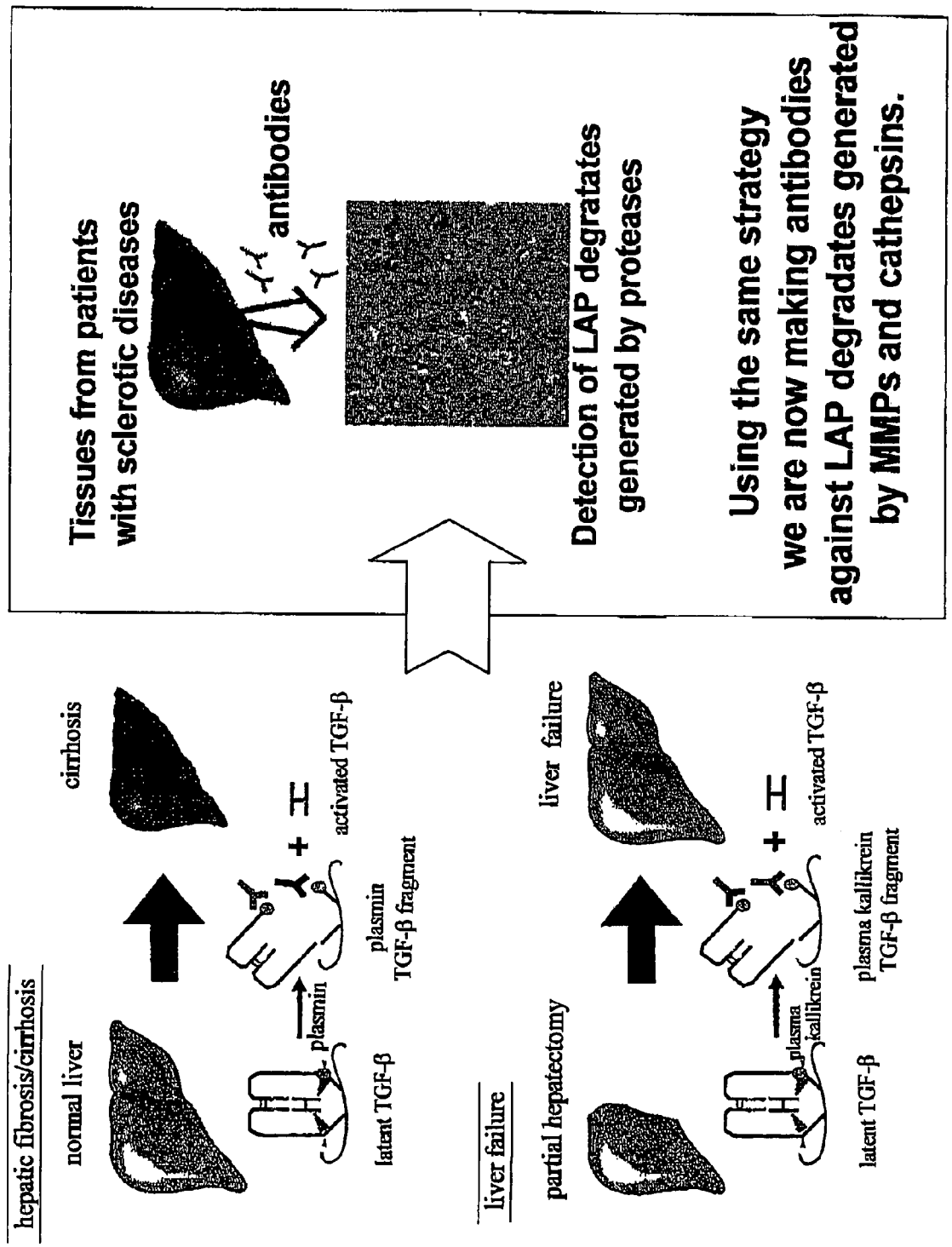

FIG. 4 shows proteolytic activation of TGF-β during pathogenesis of sclerotic diseases. The right panel shows the results of detection of an LAP degraded product generated with protease in the tissues of a patient with sclerotic disease.

Figure 5:
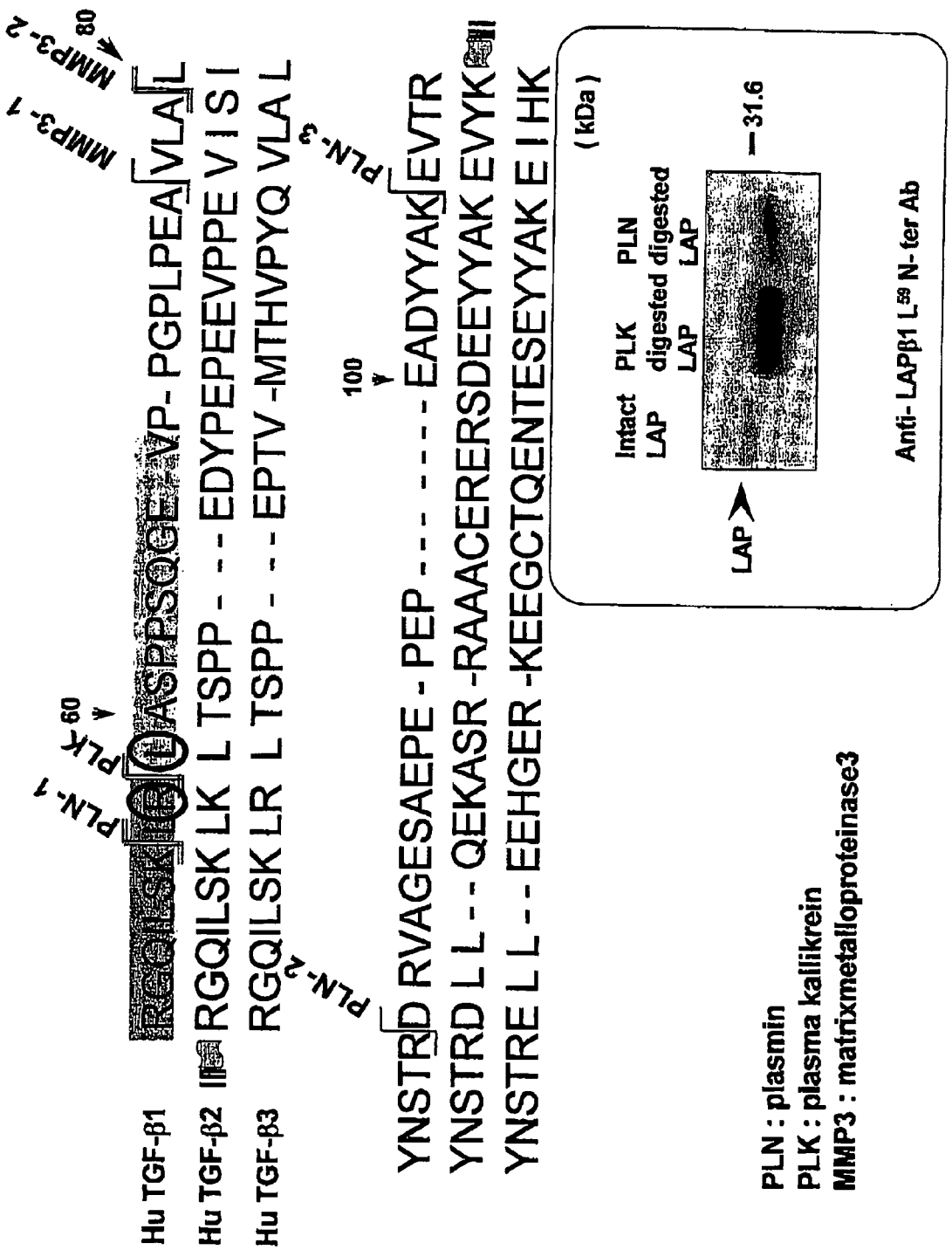

FIG. 5 shows the results of limited degradation of LAP β1 with various types of proteases, and the amino acid sequence and nucleotide sequence of human TGF-β1. FIG. 5 discloses Residues 50-110 of SEQ ID NO: 1 and SEQ ID NOS: 3-4, respectively, in order of appearance.

Figure 6:
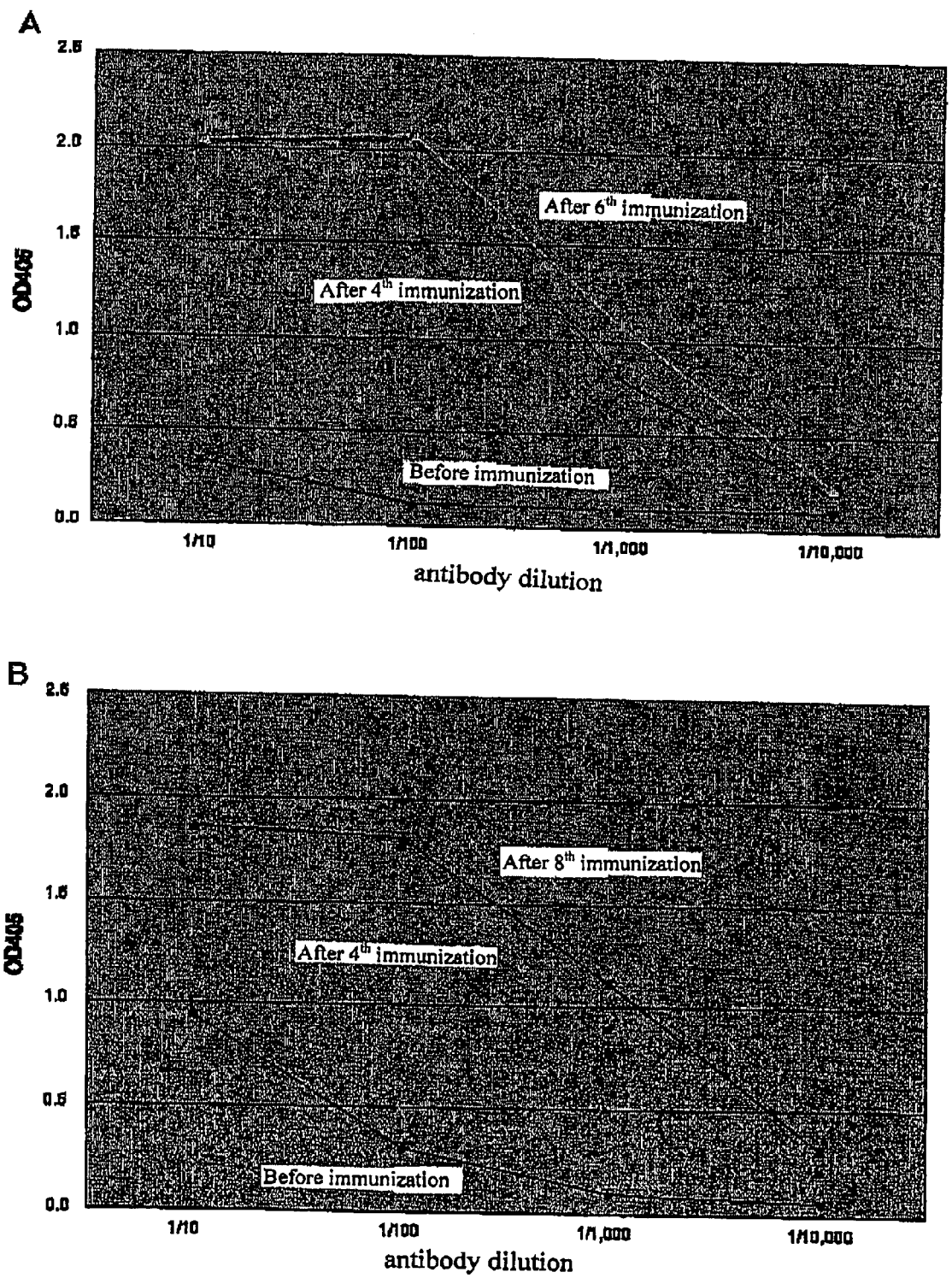

FIG. 6 shows the results of ELISA measuring the titer of the LAP peptide antibodies produced in the examples.

A: ELISA checking the titer of the antibody (2172-PLN C-ter 56Lys Ab)

B: ELISA checking the titer of the antibody (Rabbit Y-PLN N-ter 57Leu Ab)

Figure 7:
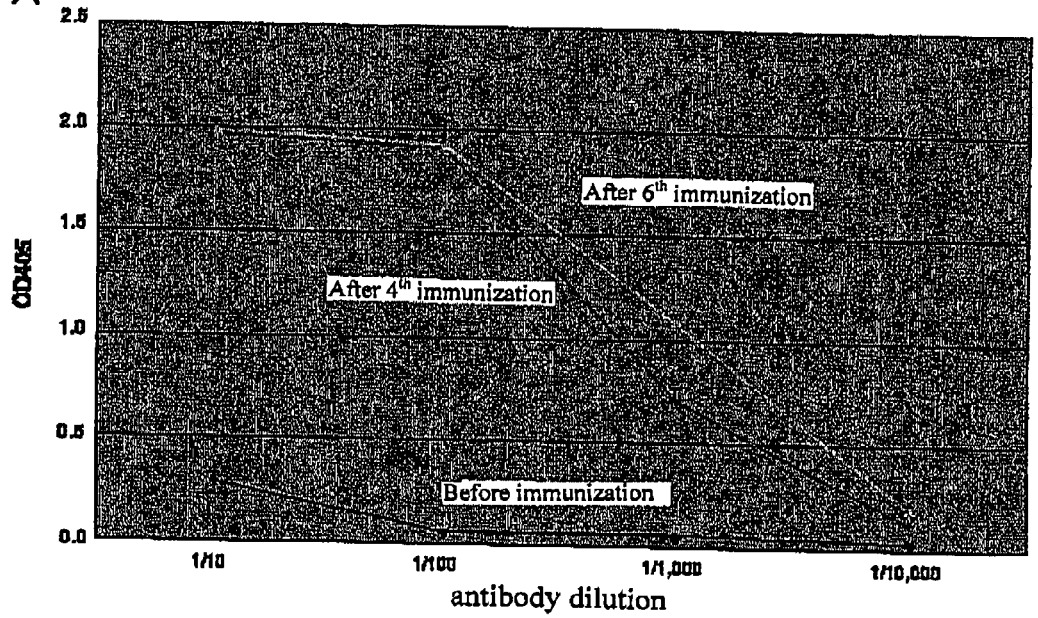
Figure 7:
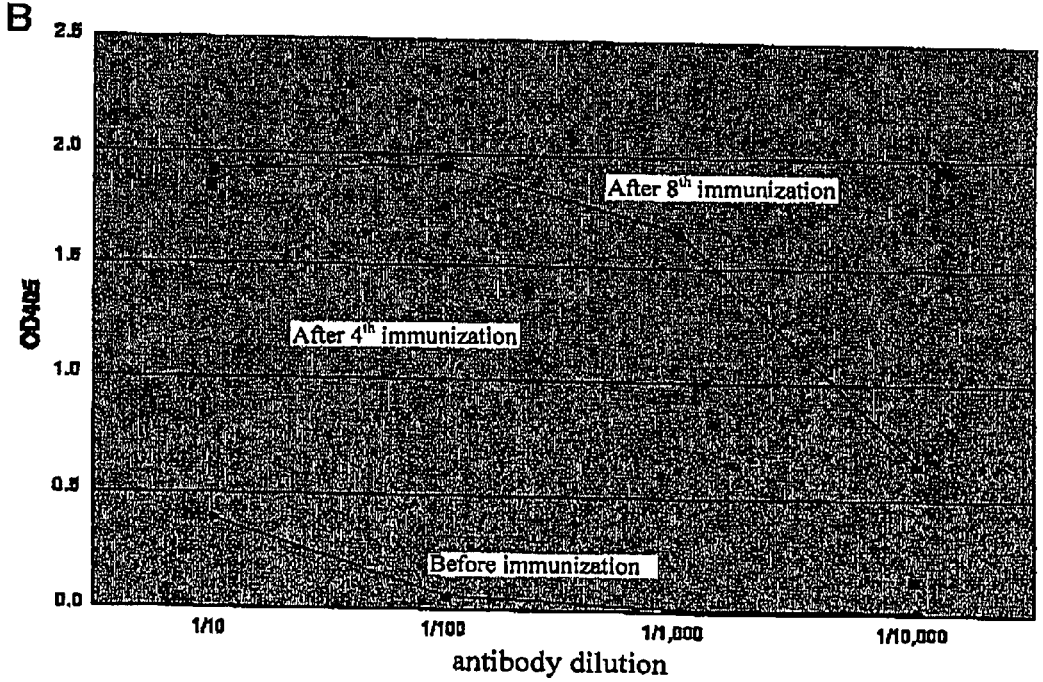

FIG. 7 shows the results of ELISA measuring the titer of the LAP peptide antibodies produced in examples.

C: ELISA checking the titer of the antibody (2173-PLKN C-ter 58Arg Ab)

D: ELISA checking the titer of the antibody (Rabbit K-PLK N-ter 59Leu Ab)

Figure 8:
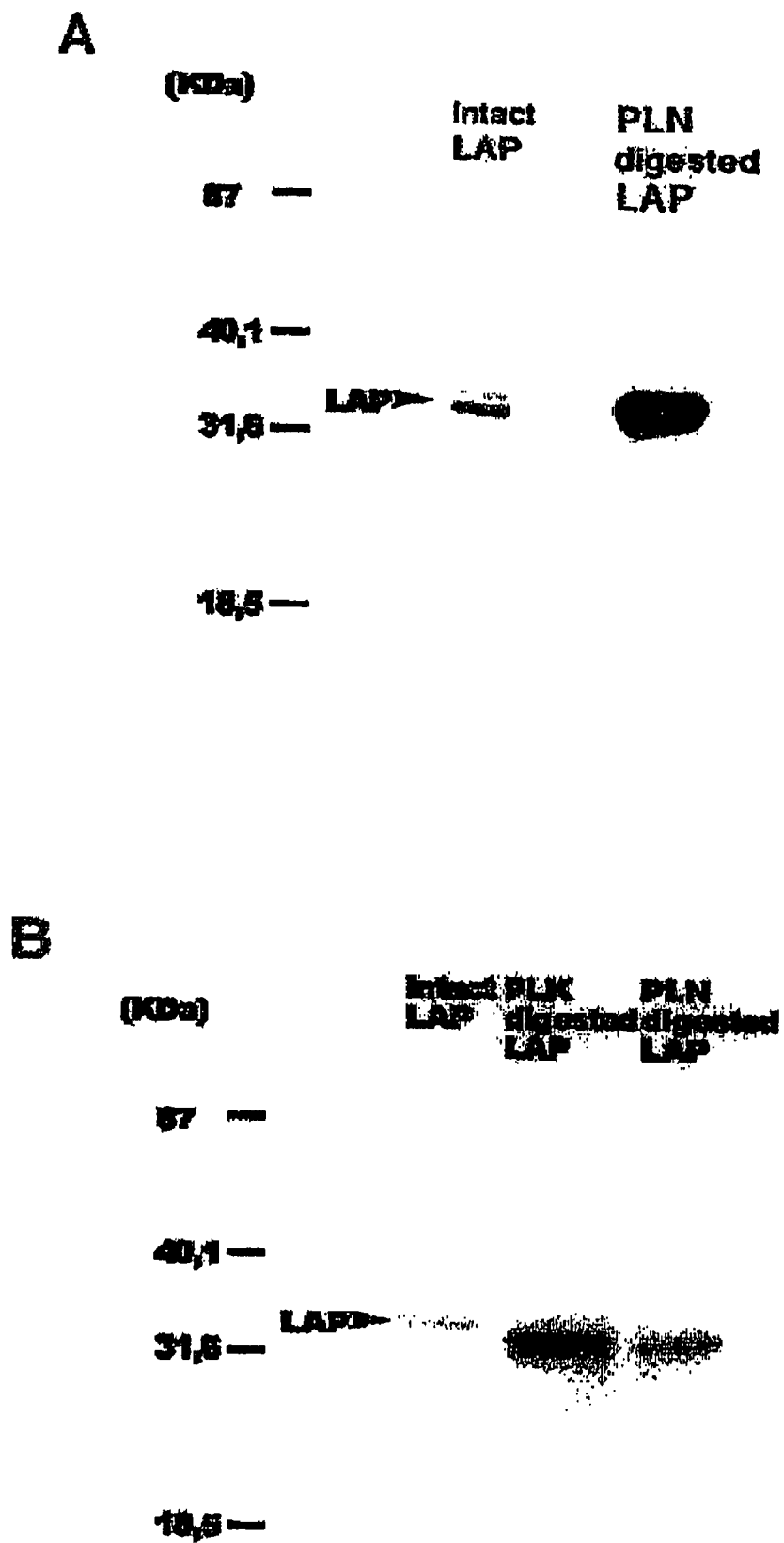

FIG. 8 shows the results of Western blot analysis using the LAP peptide antibodies.

A: PLN N-ter 57Leu Ab (1/800)

B: PLK N-ter 59Leu Ab (1/800)

Figure 9:
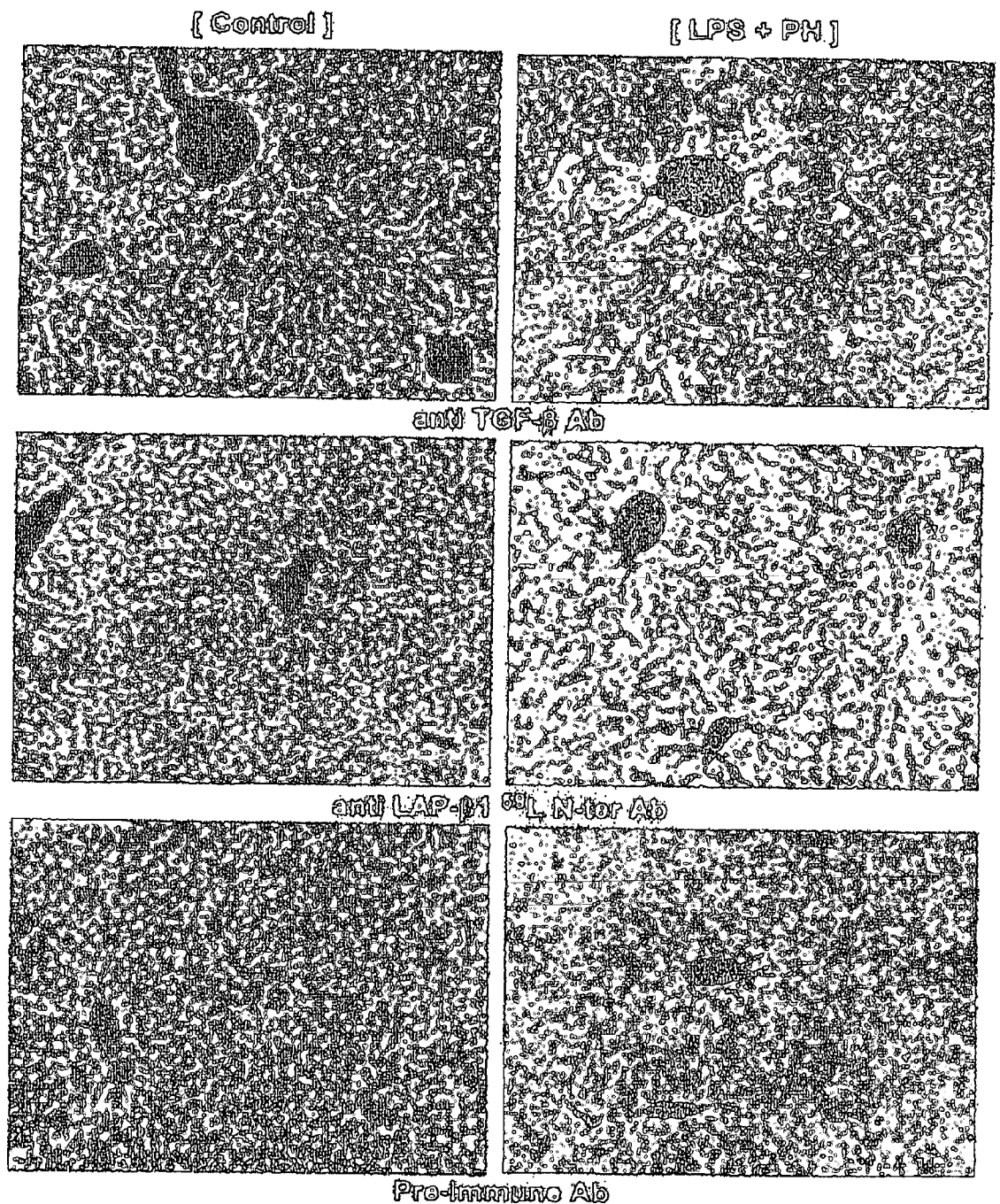

FIG. 9 shows a staining image of the liver tissue of an animal model for impaired liver regeneration.

Figure 10:
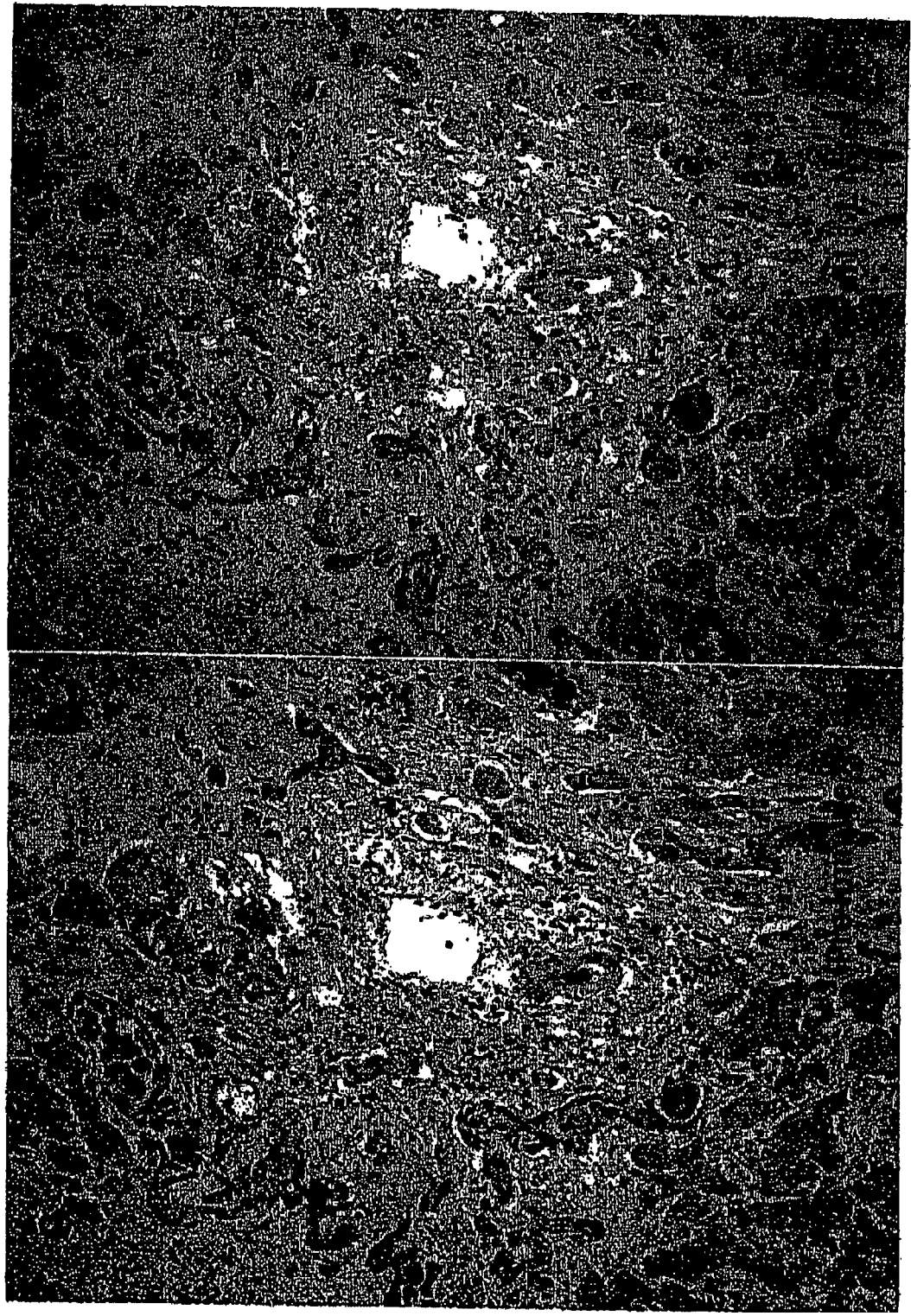

FIG. 10 shows a staining image of the liver section of a patient who died due to fulminant hepatitis.

Figure 11:
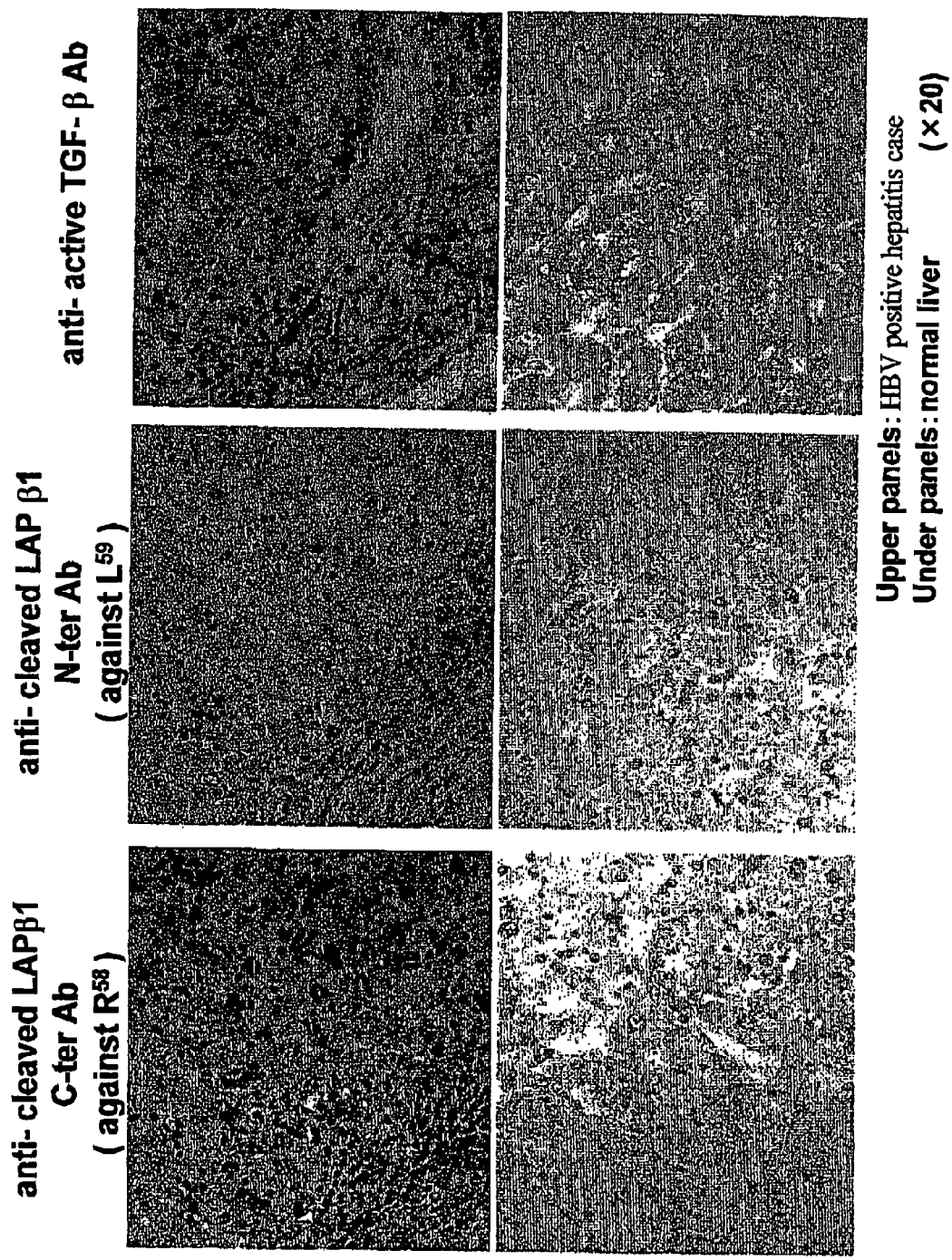

FIG. 11 shows a staining image of the liver section of a patient who died due to hepatitis B.

Figure 12:
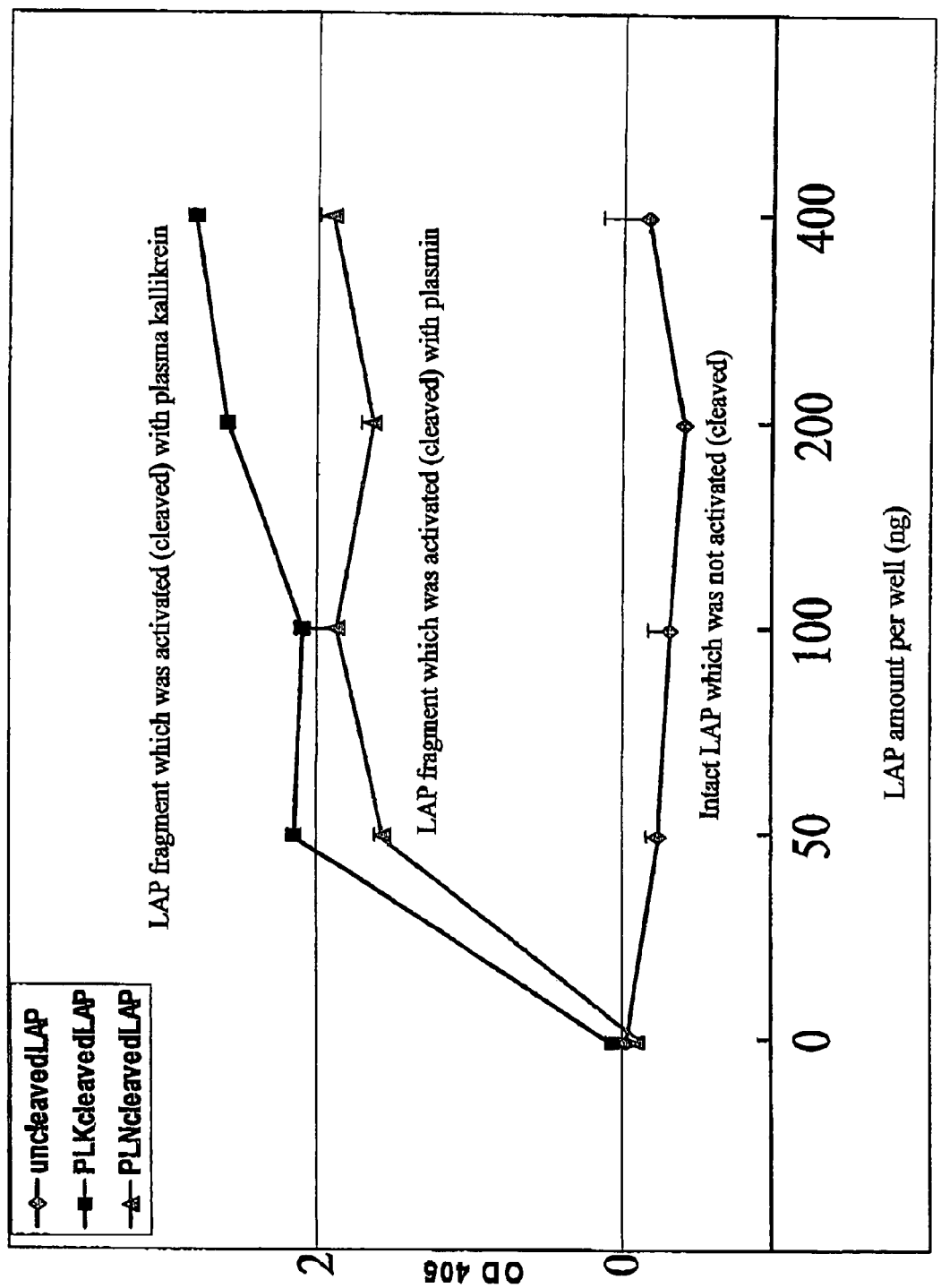

FIG. 12 shows the result of sandwich ELISA using a standard substance described in the examples.

BEST MODE FOR CARRYING OUT THE INVENTION

Figure 1:
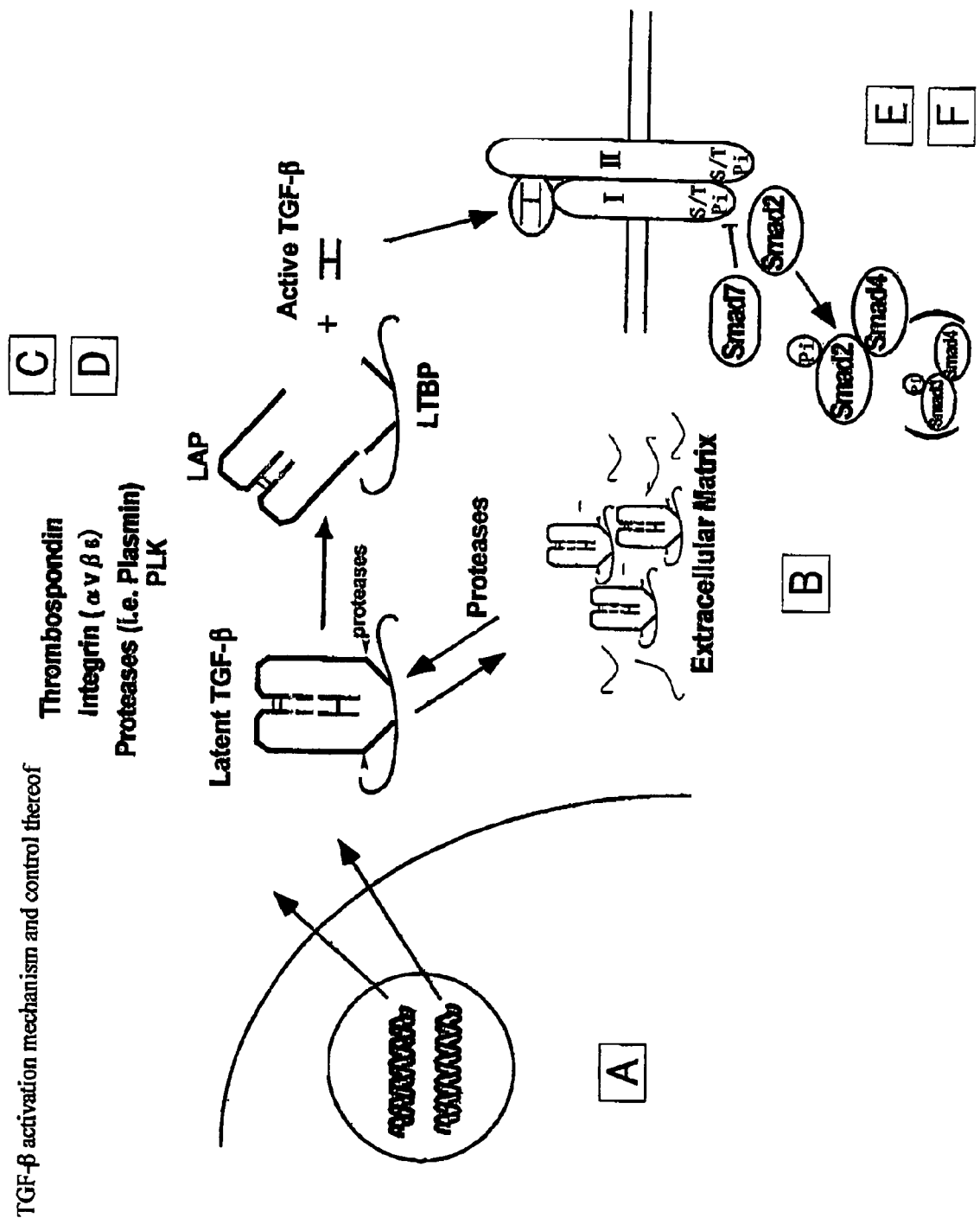
FIG. 1 shows the summary of mechanism of the TGF-β activation reaction and its regulation.

TGF-β exerts many biological activities; it plays a role in pathogenesis of sclerotic diseases and suppresses the functions of immune cells. At the same time, TGF-β suppresses excessive generation of proteases, so as to prevent lung tissue destruction, which leads to emphysema, or it suppresses the growth of cancer cells. Thus, TGF-β is a multifunctional cytokine acting as a homodimer with a molecular weight of 25 kD. TGF-β is generated as an inactive latent form with a molecular weight of approximately 300 kD, which is not able to bind to a receptor. Latent TGF-β is activated on the surface of a target cell or a peripheral area thereof and becomes an active form capable of binding to a receptor and exhibiting its functions (FIG. 1). Active TGF-β1 with a molecular weight of 25 kD is originally produced as a precursor protein consisting of 391 amino acids (the amino acid sequence thereof is shown in SEQ ID NO: 1, and the nucleotide sequence thereof is shown in SEQ ID NO: 2). Thereafter, a site between 279 Arg and 280 Ala is cleaved by the action of furin-like protease in the Golgi apparatus, and a portion consisting of 112 amino acids of the carboxyl-terminal side is dimerized by a disulfide bond, thereby generating active TGF-β1, TGF-β2 and TGF-β3 have the same structure as that of TGF-β1, and the Arg-Ala sequence is preserved among TGF-β1, TGF-β2, and TGF-β3. After cleavage, the remaining amino-terminal portion called LAP (latency associated peptide) is also dimerized (molecular weight: 75 kD). Even after LAP has been cleaved off from active TGF-β, it traps the active TGF-β through a non-covalent binding, so as to form a small latent TGF-β complex (SLC), and thereby active TGF-β still remains in a structure incapable of binding to a receptor, namely, latent TGF-β. Furthermore, in many cases, LTBP (latent TGF-β binding protein), which is a protein with a molecular weight of approximately 200 kD produced from another gene, binds to the end of a LAP dimer, so as to form a large latent TGF-β complex (LLC). TGF-β2 and TGF-β3 have the similar structure as that of TGF-β1 (FIG. 2). LTBP has a structure similar to that of fibrillin, one type of extracellular matrix protein. LLC is pooled in the extracellular matrix via the portion (FIGS. 1 and 2).

Activation of TGF-β is the reaction preventing the interaction between LAP and active TGF-β by a certain method, so as to dissociate and release the active TGF-β from LLC. TGF-β activation takes place on the surface of a target cell or a peripheral area thereof, after LLC has been released from the matrix (FIG. 1). Hitherto known physiological TGF-β activation reactions include: an adhesive activation reaction, wherein LAP binds to thrombospondin or integrin, so that the structure of LAP is altered releasing active TGF-β; and a proteolytic activation reaction, wherein LAP is limitedly cleaved by proteases releasing active TGF-β (FIG. 2). Using animal models, the present inventors have demonstrated that when serine proteases such as plasmin and plasma kallikrein are inhibited with a synthetic low-molecular-weight protease inhibitor or with a specific antibody, a TGF-β activation reaction is blocked, thereby suppressing the pathogenesis. They showed that TGF-β is activated by plasmin in the pathogenesis of hepatic fibrosis or cirrhosis, and by plasma kallikrein during the process of impaired liver regeneration (FIG. 3).

TGF-β ubiquitously exists in various tissues among our body. Its activation mechanism differs depending on the type of tissues or the conditions thereof. For example, in the lung or pancreas tissues, thrombospondin 1 functions, whereas in the lung or skin tissues having inflammation, integrin αVβ functions. Furthermore, in the liver (in particular, injured liver), serine proteases function. It has also been reported that matrix metalloproteases (MMPs) function in a cancerous portion or in the skin. Thus, it is considered that TGF-β activation is a tissue-specific mechanism controlling TGF-β functions. Moreover, the activation determines the specificity of isoforms, namely when and where, which type of isoform functions. In mammals, three types of isoforms, TGF-β1, -β2, and -β3, are generated. All of the active TGF-β portions thereof have a dimeric structure of polypeptides each consisting of 112 amino acids, and share a high homology of 71% to 82%. Thus, they express almost the same physiological activities. In contrast, since the homology of the LAP portion is low (34% to 35%), the activation mechanism differs depending on the type of an isoform. That is to say, it is considered that TGF-β activation is a posttranslational controlling mechanism for determining isoform specificity. For example, TGF-β1 and TGF-β3 have an RGD sequence in their LAP portion. However, TGF-β2 does not have such a sequence. Thus, the TGF-β isoform, which integrin binds to and activates, are TGF-β1 and TGF-β3, On the other hand, it has been reported that MMP-9 mainly acts on TGF-β2. It is predicted that different enzymes function depending on pathologic conditions, so as to generate a specific isoform of TGF-β (FIG. 2).

The present inventors have tried to determine cleavage sites by plasmin and plasma kallikrein for activation, and found that plasmin specifically cleaves between 56 Lys and 57 Leu of latent TGF-β, and plasma kallikrein specifically cleaves between 58 Arg and 59 Leu thereof, so that they cause a similar structural alteration, leading to activation of TGF-β. Subsequently, the present inventors have attempted to prepare "the protease-degraded TGF-β antibody", which specifically detects latent TGF-β fragments formed by the action of proteases. As a result, they have succeeded in production of an antibody recognizing the cutting edge ending at 57 Leu as well as an antibody recognizing the cutting edge ending at 59 Leu. The antibody recognizing the cutting edge ending at 59 Leu did not recognize an intact LAP that had not undergone an activation reaction (that had not been cleaved), but it specifically and strongly recognized the LAP fragment formed with plasma kallikrein. Moreover, by presenting that the antibody can stain the liver tissue sections of an animal model for impaired liver regeneration or the liver tissue sections of a patient who died due to fulminant hepatitis, the present inventors have succeeded, for the first time, in showing that a proteolytic TGF-β activation reaction occurs during pathogenesis in humans. Thus, the inventors have strongly suggested a high possibility that a specific inhibitor or antibody to plasma kallikrein is effective against liver failure occurring in fulminant hepatitis (FIG. 4). Subsequently, the inventors have determined the cleavage sites for MMP3. They have found that MMP3 specifically cleaves between 79 Ala and 80 Leu of latent TGF-β, so as to activate TGF-β.

In the present invention, a region (51 Gly-110 Arg), which contains cleavage sites with various proteases thereby causing activation of TGF-β, is defined as "the TGF-β activation controlling region". Specific antibodies, which recognize respective cleavage sites made by various proteases within this region, are produced. Thus, the technique has been established to specifically detect pathogenesis-, tissue-, isoform- specific active TGF-β generation reaction based on various proteolytic activation reactions, which cannot be detected using an antibody against active TGF-β or intact LAP in the prior art techniques. Using the same strategy, it is possible to produce an antibody for detecting proteolytic activation reactions by other proteases, or an antibody for detecting an adhesive activation reaction due to thrombospondin or integrin.

As stated above, the antibody of the present invention is an antibody against the LAP fragments of human TGF-β1, human TGF-β2, and human TGF-β3, which is characterized by its ability to specifically recognize the cleavage sites located within the region from the amino acid residue glycine at position 51 to the amino acid residue arginine at position 110 of human TGF-β1, and corresponding regions of human TGF-β2 and human TGF-β3.

Specific examples of the antibody of the present invention may include: an antibody specifically recognizing the cutting edge ending at the leucine residue at position 59, wherein a protease cleavage site is between the arginine residue at position 58 and the leucine residue at position 59; an antibody specifically recognizing the cutting edge ending at the arginine residue at position 58, wherein a protease cleavage site is between the arginine residue at position 58 and the leucine residue at position 59; an antibody specifically recognizing the cutting edge ending at the leucine residue at position 57, wherein a protease cleavage site is between the lysine residue at position 56 and the leucine residue at position 57; an antibody specifically recognizing the cutting edge ending at the lysine residue at position 56, wherein a protease cleavage site is between the lysine residue at position 56 and the leucine residue at position 57; an antibody specifically recognizing the cutting edge ending at the leucine residue at position 80, wherein a protease cleavage site is between the alanine residue at position 79 and the leucine residue at position 80; an antibody specifically recognizing the cutting edge ending at the alanine residue at position 79, wherein a protease cleavage site is between the alanine residue at position 79 and the leucine residue at position 80; an antibody specifically recognizing the cutting edge ending at the aspartic acid residue at position 86, wherein a protease cleavage site is between the arginine residue at position 85 and the aspartic acid residue at position 86; an antibody specifically recognizing the cutting edge ending at the arginine residue at position 85, wherein a protease cleavage site is between the arginine residue at position 85 and the aspartic acid residue at position 86; an antibody specifically recognizing the cutting edge ending at the glutamic acid residue at position 107, wherein a protease cleavage site is between the lysine residue at position 106 and the glutamic acid residue at position 107, an antibody specifically recognizing the cutting edge ending at the lysine residue at position 106, wherein a protease cleavage site is between the lysine residue at position 106 and the glutamic acid residue at position 107; an antibody specifically recognizing the cutting edge ending at the valine residue at position 77, wherein a protease cleavage site is between the alanine residue at position 76 and the valine residue at position 77; and an antibody specifically recognizing the cutting edge ending at the alanine residue at position 76, wherein a protease cleavage site is between the alanine residue at position 76 and the valine residue at position 77.

The antibody of the present invention may be either polyclonal antibodies or monoclonal antibodies, The antibodies of the present invention can be produced by a common method.

In the case of producing a polyclonal antibody against active human TGF-β1, for example, a mammal is immunized with an antigen, a peptide formed by adding a cysteine residue to the end of an LAP β1 sequence (for example, 10 amino acid residues) on the C-terminal side, which starts with the amino acid at the aforementioned protease cleavage sites, or a peptide formed by adding a cysteine residue to the beginning of an LAP β1 sequence (for example, 10 amino acid residues) on the N-terminal side, which terminates with the aforementioned protease cleavage sites, Thereafter, the blood is collected from the above mammal, and an antibody is then separated and purified from the collected blood, so as to produce the above polyclonal antibody, For examples, mammals such as a mouse, a hamster, a guinea pig, a chicken, a rat, a rabbit, a dog, a goat, a sheep or a bovine, can be immunized. As such an immunization method, a common immunization method known to persons skilled in the art can be used. For example, an antigen is administered to such a mammal one or more times.

An antigen can be administered at intervals of 7 to 30 days, and particularly at intervals of 12 to 16 days, for 2 to 14 times. As a guideline of dosage, approximately 0.05 to 2 mg of antigen can be administered once, for example. An administration route is not particularly limited, but it can appropriately be selected from among subcutaneous administration, intracutaneous administration, intraperitoneal administration, intravenous administration, and intramuscular administration. It is preferable that an antigen be administered by intravenous, intraperitoneal, or subcutaneous injection. In addition, an antigen can be dissolved in suitable buffer solution that contains a commonly used adjuvant such as a complete Freund's adjuvant, RAS [MPL (Monophosphoryl Lipid A)+TDM (Synthetic Trehalose Dicorynomycolate)+CWS (Cell Wall Skeleton) adjuvant system], or aluminum hydroxide, and it can be then used. However, depending on an administration route or other conditions, there may be cases where the aforementioned adjuvants are not used. The term "adjuvant" is used herein to mean a substance for non-specifically reinforcing an immune reaction on an antigen, when it is administered together with the antigen.

After an immunized mammal has been bred for 0.5 to 4 months, a small amount of the serum of the above mammal was sampled from the ear vein thereof, and the titer can be determined. If the titer of the antibody increases, an antigen is administered suitable times, depending on the situation. For example, a booster can be carried out using 10 to 1,000 µg of antigen, The blood is collected from the immunized mammals by a common method, 1 or 2 months after the final administration. Thereafter, the collected blood is separated and the antibody is purified by common methods such as centrifugation, precipitation using ammonium sulfate or polyethylene glycol, or several types of chromatography such as gel filtration chromatography, ion exchange chromatography, or affinity chromatography, so as to obtain the polyclonal antibody of the present invention in the form of a polyclonal antiserum. The serum may be treated at 56° C. for 30 minutes, for example, so as to inactivate the complement system thereof.

When the antibody of the present invention is a monoclonal antibody, the globulin type of the monoclonal antibody is not particularly limited. Examples of a globulin type may include IgQ IgM, IgA, IgE, and IgD. In addition, the monoclonal antibody of the present invention may be either a humanized antibody or a human antibody.

A cell line for generating the monoclonal antibody of the present invention is not particularly limited. For example, antibody-generating cells and a myeloma cell line are subjected to cell fusion, so as to obtain a hybridoma. Such a hybridoma for generating the monoclonal antibody of the present invention can be obtained by the following cell fusion method.

Splenic cells, lymph node cells, B lymphocytes, and other cells collected from an immunized animal can be used as antibody-generating cells. As an antigen, the same peptide as in the case of a polyclonal antibody can be used, As an animal to be immunized, a mouse, a rat or the like, is used. An antigen is administered to such an animal by a common method, For example, a suspension or an emulsified liquid, which comprises an adjuvant such as a complete Freund's adjuvant or an incomplete Freund's adjuvant and an antigen peptide, is prepared. Such a suspension or an emulsified liquid is administered to an animal, several times, via an intravenous, subcutaneous, intracutaneous, or intraperitoneal route, so as to immunize the animal. Thereafter, splenic cells are obtained as antibody-generating cells from the immunized animal, for example. The thus obtained cells are fused with myeloma cells by a known method (G. Kohler et al., Nature, 256 495 (1975)), so as to prepare a hybridoma.

Examples of a myeloma cell line used in cell fusion may include a mouse P3X63Ag8 strain, P3U1 strain, and Sp2/0 strain. For cell fusion, a fusion promoter such as polyethylene glycol or Sendai virus is used. In order to select a hybridoma after completion of the cell fusion, hypoxanthine aminopterin thymidine (HAT) culture medium can be used according to a common method. A hybridoma obtained as a result of the cell fusion can be cloned by the limiting dilution method or the like. Moreover, the cloned hybridomas are screened by enzyme immunoassay or the like, so as to obtain a cell line for generating a monoclonal antibody which specifically recognizes an LAP fragment generated along with the generation of active human TGF-β1.

In order to produce a monoclonal antibody of interest from the above obtained hybridoma, they are cultured by a common cell culture method or ascites formation method, and the above monoclonal antibody may be then purified from a culture supernatant or ascites. Such a monoclonal antibody can be purified from a culture supernatant or ascites by a common method. For example, methods such as ammonium sulfate fractionation, gel filtration, ion exchange chromatography, or affinity chromatography can be used in combination, as appropriate.

Furthermore, the fragments of various types of antibodies as described above are also included in the scope of the present invention. Examples of such an antibody fragment may include an F(ab')2 fragment and a Fab' fragment.

The antibody of the present invention can also be used as a labeled antibody, By preparing such a labeled antibody, it becomes possible to easily carry out the detection or measurement of the activation reactions of human TGF-$\beta$1, human TGF-$\beta$2, and human TGF-$\beta$3. The type of a labeling substance that labels an antibody and a labeling method can be appropriately selected from those known to persons skilled in the art.

When an enzyme is used as a labeling substance, examples of such an enzyme used herein may include horseradish peroxidase, alkaline phosphatase, glucose oxidase, $\beta$-galactosidase, glucoamylase, carbonic anhydrase, acetylcholine esterase, lysozyme, maleate dehydrogenase, malate dehydrogenase, and glucose-6-phosphate dehydrogenase. Examples of a method for labeling the antibody of the present invention or a fragment thereof (F(ab')2 fragment, Fab' fragment, etc.) with such an enzyme may include: a method of oxidizing the sugar chain of the enzyme with periodic acid and then allowing amino acid of the above antibody to bind to the generated aldehyde group; and a method of introducing a maleimide group, a pyridylsulfide group or the like into an enzyme, and allowing the enzyme to bind to a thiol group existing in a Fab' fragment of the above antibody.

When an enzyme is used as a labeling substance, a test sample and a labeled antibody are incubated, and the released labeled antibody is then eliminated by washing. Thereafter, a substrate of the aforementioned labeling enzyme is allowed to act thereon, and the reaction is measured based on coloration or the like, so as to detect a labeled antibody. When an antibody is labeled with peroxidase, for example, hydrogen peroxide acting as a substrate combines with diaminobenzidine or O-phenylenediamine acting as a coloring reagent, so as to develop a brown or yellow color. When an antibody is labeled with glucose oxidase, 2,2'-azino-di-(3-ethylbenzothiazoline-6-sulfonic acid (ABTS) is used as a substrate, for example.

When a fluorescent dye is used as a labeling substance, the antibody of the present invention or a fragment thereof can be labeled with a fluorescent dye such as FITC (fluorescein isothiocyanate) or TRITC (tetramethylrhodamine B isothiocyanate). The antibody of the present invention or a fragment thereof is allowed to bind to a fluorescent dye by a common method.

When a color labeling substance is used as a labeling substance, a colloidal metal, a color latex, or the like can be used as such a labeling substance, for example. Representative examples of such a colloidal metal may include metal colloidal particles, which are the disperse particles of gold sol, silver sol, selenium sol, tellurium sol, and platinum sol. The particle diameter of the colloidal metal is generally between approximately 3 and 60 nm. A representative example of such a color latex is a synthetic latex such as a polystyrene latex colored with a red or blue pigment. As such a latex, a natural latex such as a natural rubber latex can also be used. The size of such a color latex can be selected from the diameter range between several tens of nm and several hundreds of nm. A commercially available product can directly be used as such a color labeling substance. However, in some cases, such a commercially available product can be further processed. Otherwise, such a color labeling substance can also be produced by a known method.

The antibody of the present invention or a fragment thereof is allowed to bind to a color labeling substance by a common method. When such a color labeling substance is a gold colloidal particle that is the disperse particle of gold sol, for example, an antibody is generally mixed with the gold sol at room temperature, so as to physically bind them.

For labeling, affinity labeling (for example, biotin, etc.), isotopic labeling (for example, $^{125}$I, etc.), or the like can also be used, as well as the aforementioned labeling methods.

The enzyme antibody technique, immunohistochemical staining, immunoblotting, direct immunofluorescence, or indirect immunofluorescence, wherein the labeled antibody of the present invention is used, can be carried out by a method known to persons skilled in the art. The experimental conditions therefor can also be appropriately selected by persons skilled in the art.

Using the antibody of the present invention, the activation reactions of human TGF-$\beta$1, human TGF-$\beta$2, and human TGF-$\beta$3 can be detected or measured in a biological sample or tissue, thereby diagnosing TGF-$\beta$-associated diseases including sclerotic diseases as typical examples, Such a method for detecting or measuring the activation reactions of human TGF-$\beta$1, human TGF-$\beta$2, and human TOP-$\beta$3, and a method for diagnosing TGF-$\beta$-associated diseases including sclerotic diseases as typical examples, are also included in the scope of the present invention.

The antibody of the present invention enables of the detection or measurement of the activation reactions of human TGF-$\beta$1, human TGF-$\beta$2, and human TGF-$\beta$3 in living bodies. Thus, TGF-$\beta$-associated diseases including sclerotic diseases as typical examples can be diagnosed. That is to say, the antibody of the present invention is useful as a diagnostic agent for TGF-$\beta$-associated diseases including, as typical example, sclerotic diseases (for example, hepatic fibrosis/cirrhosis, atherosclerosis, lung fibrosis, scleroderma, renal failure, etc.) caused by active human TGF-$\beta$1, human TOP-$\beta$2, and human TGF-$\beta$3.

The present invention will be more specifically described in the following examples. However, these examples are not intended to limit the scope of the present invention.

EXAMPLES

First, the entire summary of the examples will be explained. Human recombinant LAP $\beta$1 was cleaved with various types of proteases such as human plasma kallikrein (PLK), human blood-derived plasmin, and human recombinant matrix metalloprotease 3 (MMP3). Thereafter, the amino acid sequence of each cleavage site was determined. A peptide including a cleavage site was synthesized, so as to prepare an antigen peptide. A rabbit was immunized with an antigen peptide which was bound to a typical carrier protein, KLH (Keyhole Lympet Hemocyanin) via a thiol group of a cysteine residue imported to the side opposite to the cutting edge of the above antigen peptide. Four weeks after the initial immunization, an antiserum was collected, and generation of an antibody of interest was then assessed by ELISA. After an increase in the antibody titer had become stable, a specific peptide antibody was purified with Sepharose resins on which antigen peptides had been immobilized. Further, peptide sequence-recognizing antibodies were eliminated from the above peptide antibodies, so as to obtain cutting edge-recognizing antibodies of interest (which are antibodies that specifically recognize a proteolytic cleavage site within LAP $\beta$1). The specificity of the obtained cutting edge-recognizing antibody was confirmed by Western blotting. Furthermore, the staining profiles of liver tissue sections from an animal model for impaired liver regeneration and a patient who died due to fulminant hepatitis were evaluated.

Example 1

Limited Degradation of LAP β1 with Various Proteases

Eight hundred ng of human recombinant LAP β1 (R&D) was incubated at 37° C. for 0 to 30 minutes in 27 μl (total amount) of PBS buffer, together with human plasma kallikrein (Sigma) at a final concentration of 222.2 μm/ml, human blood-derived plasmin (PLN) (Sigma) at a final concentration of 111.1 μm/ml, and human recombinant matrix metalloprotease 3 (MMP3) (Alexis) at a final concentration of 6 μg/ml. Thereafter, the resultant fragments were separated by 12.5% polyacrylamide gel electrophoresis, and degradation was then confirmed using a silver staining kit of Wako Pure Chemical Industries, Ltd.

Example 2

Determination of Limited Degradation Site and Discovery of TGF-β Activation Controlling Region LAP β1 fragments (200 to 400 ng), which had been limitedly degraded with various proteases, were separated by SDS-12.5% polyacrylamide gel electrophoresis according to the method of Laemmli (*Nature* 227, 680 (1970)). Thereafter, proteins existing on the gel were transcribed on a PVDF (polyvinylidene fluoride) membrane by electrophoresis, and were then visualized with a CBB (Coomassie blue R-250) dye. A protein band visualized on the PVDF membrane was cut out, and subjected to the reaction layer of a micro pulsed liquid phase protein sequencer (Procise 494cLC; manufactured by Applied Biosystems). Thereafter, Edman degradation was carried out using the standard program. Thus, PTH (phenylthiohydantoin)-amino acid, which was successively cut out of the N-terminus in each cycle, was identified based on the elution time of chromatography. The sequence of 10 residues at the N-terminus of each fragment as limitedly decomposed above was determined, so as to determine each limited cleavage site. As a result, it was found that plasmin specifically cleaves between 56 Lys and 57 Leu of latent TGF-β, that plasma kallikrein specifically cleaves between 58 Arg and 59 Leu thereof, and that MMP3 specifically cleaves between 79 Ala and 80 Leu thereof, suggesting that they cause a similar structural change, leading to the activation of TGF-β (FIG. 5). Further, when incubation was carried out for a longer period of time, plasmin successively cleaved between 85 Arg and 86 Asp, and between 106 Lys and 107 Glu. A region (51 Gly-110 Arg), which is cleaved with proteases leading activation reaction, was defined as a TGF-β activation controlling region.

Example 3

Production of Antigen Peptide

A peptide formed by adding a cysteine residue to the end of the C-terminal LAP β1 sequence (10 amino acid residues) starting with amino acid of the above determined cleavage site, or a peptide formed by adding a cysteine residue to the beginning of the N-terminal LAP β1 sequence (10 amino acid residues) terminating with the cleavage site, was synthesized by the Fmoc method for solid phase synthesis (synthesizer: PSSM-8 manufactured by Shimadzu Corporation). As deprotecting agents, ethanedithiol/thioanisole/trifluoroacetic acid were used. In order to import antigenicity to the synthetic peptide, hemocyanin (keyhole limpet hemocyanin; KLH) (manufactured by Sigma) was allowed to bind thereto as a earner protein. An amino group contained in KLH was modified with m-maleimidebenzoyl-N-hydroxysuccinimide ester (PMBS), and the synthetic peptide that contained a cysteine residue was then allowed to react with the thus modified group, so as to covalently bind them. Ten μl of 0.3 mg/μl MBS dimethylformamide solution was added dropwise to 1.25 ml of a 10 mM sodium phosphate buffer (pH 7.2), in which 20 mg of hemocyanin had been dissolved. Thereafter, the mixture was stirred at room temperature for 30 minutes, so as to bind them each other. After precipitates had been removed by centrifugation, supernatant was subjected to a sephadex G25 gel filtration column. Thereafter, 50 mM sodium phosphate buffer (pH 6.0) was flown over it, so as to separate unreacted MBS from MBS-bound KLH. The MBS-bound KLH fraction was identified with CBB, and it was used in an amount of 100 μg each. One mg of the synthetic peptide dissolved in 0.5 ml of distilled water and 0.2 M sodium phosphate buffer (pH 7.4) containing half amount of the MBS-bound KLH solution were mixed, and the obtained mixture was then stirred at room temperature for 3 hours, so as to allow KLH to bind to a cysteine residue of each peptide via an NHS ester of MBS.

Example 4

Immunization of Rabbit and Collection of Blood

A rabbit (female, approximately 2 kg, New Zealand White, KITAYAMA LABES Co., Ltd.) was purchased, and then left for 1 week, so as to acclimatize to the environment. After the blood (10 ml) had been collected from the rabbit before immunization, an emulsion prepared by homogenizing a KLH-peptide antibody solution containing 100 μg of the synthetic peptide and 100 μl of a complete adjuvant of RIBI via a metal contact was injected into several tens of points of the back of the rabbit for immunization. From 4 weeks after the initial immunization, blood collection of 10 ml each and booster were repeated every week until the $14^{th}$ week. Thereafter, exsanguination was conducted from the heart. Blood collection was carried out alternatively from the left and right ear vein. A $\frac{1}{10}$ amount of 3.8% sodium citrate solution was used as an anticoagulant. The collected blood was centrifuged at 4° C. for 30 minutes at 10,000 rpm to eliminate blood cell components, thereby obtaining blood plasma. A calcium chloride solution at a final concentration of 10 mM was added to the obtained blood plasma, and the mixture was left at rest at 4° C. overnight for consolidation. Thereafter, the coagulated components were eliminated by centrifugation (4° C., 15 minutes, 10,000 rpm), so as to collect antiserum.

Example 5

Confirmation of Generation of Antibody

A change in the antibody titer in each antiserum was measured by ELISA (Enzyme-Linked Immuno-Sorbent Assay) using various types of antigen peptides, to which BSA had been conjugated. BSA-bound peptide was prepared by the same method as for the KLH-bound peptide used as an antigen. BSA-bound peptide was diluted with 50 mM carbonate buffer (pH 9.6) to a concentration of 4 μg/ml. A hundred μl of the obtained dilute was poured into each well of a 96-well immunoplate (manufactured by Nunc), and then incubated at 4° C. overnight, so that the plate was coated with the BSA-bound peptide. The plate was washed with PBS-0.05% Tween 20 three times, and each antiserum was then diluted with PBS-0.05% Tween 20, so as to prepare dilution series. The prepared dilution series were added in an amount of 100 µl each, followed by incubation at 37° C. for 2 hours. The remainings were washed with PBS-0.05% Tween 20 three times, and an alkaline phosphatase-bound goat anti-rabbit antibody (manufactured by Jackson; diluted with 7,500-fold PBS-0.05% Tween 20) was added in an amount of 100 µl each, followed by incubation at 37° C. for 2 hours again. The remainings were washed with PBS-0.05% Tween 20 three times, and 200 µl each of a 1 mg/ml p-nitrophenyl phosphate-containing diethanolamine buffer was added thereto, and the mixture was incubated at 37° C. for 1 hour. Thereafter, the level of yellow coloration was determined by measuring the absorbance at 405 nm.

FIGS. 6 and 7 show the data regarding the C-terminal cutting edge (56 Lys) antibody of the plasmin (PLN) cleavage site (56 Lys-57 Leu) (FIG. 6A), the N-terminal section (57 Leu) antibody thereof (FIG. 6B), and the C-terminal cutting edge (58 Arg) antibody of the plasma kallikrein (PLK) cleavage site (58 Arg-59 Leu) (FIG. 7C), and the N-terminal cutting edge (59 Leu) antibody (FIG. 7D) thereof. After the 4 h immunization, an increase in the antibody titer was observed, and thereafter, a high antibody titer was maintained.

Example 6

Purification of Specific Peptide Antibody

Sepharose resins, on which antigen peptides had been immobilized, were prepared, and an antiserum was then adsorbed thereon, so as to purify a peptide antibody from the antiserum. One ml of slurry containing 50% epoxy-activated Sepharose resins (Pharmacia Biotech) swollen with distilled water was allowed to react with 1 mg of each type of antigen peptide at 45° C. overnight in 4 ml of binding buffer (50 mM carbonate buffer, pH 8), so as to allow the antigen peptide to bind to the Sepharose resin. The resultant was incubated at 45° C. overnight in 0.1 M monoethanolamine-containing 50 mM Tris-HCl buffer (pH 8), so as to block unreacted functional groups. Thereafter, the resultant was alternatively washed with a 0.5 M sodium chloride-containing 0.1 M acetate buffer (pH 4) and with a 0.5 M sodium chloride-containing binding buffer 3 times each, so as to prepare Sepharose resins on which the antigen peptides had been immobilized. One ml of the peptide-bound Sepharose resin and 5 ml of the recovered antiserum were stirred at 4° C. overnight, so that the peptide antibodies present in the antiserum was allowed to bind to the resins. Thereafter, the resins were washed with TBS buffer (a 0.15 M sodium chloride-containing 20 mM Tris-HCl buffer; pH 7.5), washing buffer (a 20 mM Tris-HCl buffer that contained 1 M sodium chloride and 1% Triton X-100; pH 7.5), the TBS buffer, and 0.15 M sodium chloride solution. Thereafter, the antibodies were eluted in a glycine buffer (pH 2.5). In order to immediately neutralize the antibody solution, 1 M Tris buffer with 1/20 volume of an elution volume had previously been added to the recovery fraction. The concentration of the obtained antibody was determined with a BCA assay kit (Pierce).

Example 7

Purification of Cleavage Site Section-Recognizing Antibody (Elimination of Peptide Sequence-Recognizing Antibody)

Resins were prepared by acetylating and blocking the terminus of the section of a peptide that had been immobilized on the aforementioned Sepharose resins. Peptide antibodies were passed through a column filled with the thus obtained resin, so as to eliminate peptide sequence-recognizing antibodies and purify only cutting edge-recognizing antibodies. For such acetylation, the peptide-immobilized Sepharose resins were stirred at room temperature for 5 minutes twice in 0.12 g of acetyl imidazole/4 ml dimethylformamide, The resultant was washed with dimethylformamide, and it was then charged into a spin column (column volume: 1 ml). Thereafter, 100 µg of the peptide antibodies as purified above were passed through the above spin column, so as to eliminate a peptide sequence-recognizing antibody and recover a non-adsorption fraction. The recovered fraction was defined as a cleavage site section-recognizing antibody. The protein concentration of the obtained antibody was determined with a BCA assay.

Example 8

Confirmation of Recognition Specificity of Cleavage Site Section-Recognizing Antibody The recognition specificity of the obtained cleavage site section-recognizing antibody was confirmed by Western blot analysis. FIG. 8A shows the results obtained using an antibody that recognizes the N-terminal cutting edge (57 Leu) of the plasmin cleavage site (56 Lys-57 Leu). FIG. 8B shows the results obtained using an antibody that recognizes the N-terminal cutting edge (59 Leu) of the plasma kallikrein cleavage site (58 Arg-59 Leu).

In FIG. 8, 800 ng each of human recombinant LAP β1 that had not been treated with protease, LAP β1 obtained by incubation with plasma kallikrein at a final concentration of 222.2 µg/ml at 37° C. for 30 minutes for cleaving, LAP β1 obtained by incubation with plasmin at a final concentration of 111.1 µg/ml at 37° C. for 10 minutes for cleaving, was separated through 12.5% polyacrylamide gel electrophoresis. The resultant was then electronically transferred to a PVDF (polyvinylidene fluoride) membrane. The Western blot analysis of a protein on the membrane was carried out by a known method using, in combination, rabbit antibody recognizing N-terminal cutting edge of plasmin cleavage site or recognizing N-terminal cutting edge of plasma kallikrein cleavage site (final concentration: 3.25 µg/ml) and a horseradish peroxidase-bound goat anti-rabbit IgG antibody (final dilution: 1:1, 500) (Okuno M. et al., Gastroenterology 2001; 120: 1784-1800). The band was detected with Amersham-Pharmacia (Buckinghamshire, UK) ECL system.

The antibody recognizing N-terminal cutting edge of plasma kallikrein (59 Leu) hardly recognized intact LAP β1, which had not undergone an activation reaction (which had not been cleaved) (Lane 1). The above antibody strongly recognized only the LAP β1 fragment, which had been cleaved with plasma kallikrein (PLK) (Lane 2), and it weakly recognized the plasmin (PLN) cleaved LAP β1 fragment, which had been cleaved between 56 Lys and 57 Leu that were two residues before the plasma kallikrein cleavage site (a portion between 58 Arg and 59 Leu) (Lane 3). These results show that the antibody recognizing N-terminal cutting edge of plasma kallikrein cleavage site specifically detects the cutting edge of latent TGF-β that has been degraded with plasma kallikrein.

Example 9

Confirmation of Usefulness in an Animal Model for Impaired Liver Regeneration

In order to evaluate the usefulness of the antibody recognizing N-terminal cutting edge of the plasma kallikrein cleavage site in tissue immunostaining, a mouse model for impaired liver regeneration was produced by preadministration with endotoxin (LPS) before partial hepatectomy, which had been known as an animal model in which plasma kallikrein-dependent TGF-β activation reaction is a cause for pathogenesis (Akita et al., Gastroenterology 123: 352-364, 2002). Using this mouse model, the staining properties of the antibody were examined (FIG. 9).

$C_3H$/HeN mice (5-week-old, CLEA Japan Inc., Tokyo, Japan) were isolated for 1 week. Thereafter, the mice were randomly divided into several groups consisting of 10 mice. Fifty μl of normal saline solution (either containing or not containing LPS (*Escherichia coli* 0111: B4, Sigma Chemical Co. (St. Louis, Mo.)) at a 500 ng/g of body weight) was administered to each mouse via an intraperitoneal injection. Twenty-four hours later, 67% partial hepatectomy or sham operation was performed for each mouse in accordance with the method of Higgins and Anderson (Higgins G. M. et al., Arch Pathol 1931; 12: 186-202). Forty-eight hours after the operation, the mice were sacrificed by exsanguination from the inferior vena cava under ether anesthesia. Thereafter, the liver was rapidly excised, and it was then fixed with 10% buffered formalin [formalin (37% paraformaldehyde 3% ethanol aqueous solution), which had been diluted 10-fold with PBS] at 4° C. for 24 hours. Thereafter, the remaining liver dehydrated with alcohol series, and substituted with xylol, and then embedded in paraffin using an automatic embedding device, and placed in a mold, so as to prepare liver tissue paraffin-embedded blocks. A section with a thickness of 5 μm was prepared from paraffin-embedded blocks of liver tissue using a microtome, and then used for tissue immunostaining. The paraffin was removed using xylene for 10 minutes twice, and the residue was then rinsed with each of 10%, 70%, and 50% ethanols. The resultant was washed with water and then subjected to air drying. Thereafter, a circle was drawn with a DAKO Pen (DAKO Cytomation, Kyoto, Japan) around the section, and it was further subjected to air drying for several minutes. Thereafter, it was immersed in a mixed solution consisting of dehydrated ethanol: 3% hydrogen peroxide solution (9:1), so as to block endogenous peroxidase activity. Subsequently, the resultant was stained using the Vectastain ABC elite kit (Vector Laboratories, Burlingame, Calif.) for coloration. After incubation with a blocking solution included in the kit, the resultant was placed in a wet chamber together with a primary antibody (mouse anti-TGF-β monoclonal antibody (the upper panels in FIG. 9) or the antibody recognizing N-terminal cutting edge of the plasma kallikrein cleavage site (the middle panels in FIG. 9); a final concentration of 13 μg/ml in phosphate buffered saline (PBS)), followed by incubation at 4° C. overnight. A preimmune antibody of the same rabbit was used as a control (the lower panels in FIG. 9), After washing with PBS, the section was allowed to successively react with a biotinylated secondary antibody and then with an avidin DH-biotinylated peroxidase mixed solution according to the instructions, so as to stain the section. The section was colorated with diaminobenzidine tetrahydrochloride, and the nucleus was counterstained with hematoxylin. The section was lightly rinsed with water, followed by air drying. Thereafter, it was rinsed with each of 50%, 70%, and 100% ethanol, and was then immersed once with xylene for 10 minutes. The section was mounted on a slide glass with a water-insoluble encapsulating agent, and subjected to microscopic observation.

In the control group, to which normal saline solution had been preadministered and the sham surgery had been performed; the staining signals were not obvious with any antibodies (the left side panels in FIG. 9). Also, in the group, to which a normal saline solution had been administered and the partial hepatectomy had been performed, and in the group, to which LPS had been administered and the sham surgery had been performed, the staining signals were also hardly detected. In contrast, in the group, to which LPS had been administered and the partial hepatectomy had been performed, strong staining images were detected with the TGF-β antibody around hepatic stellate cells in a perisinusoidal portion, and weak staining images were detected in hepatocytes over the above images (the right upper case panel in FIG. 9). With the antibody recognizing N-terminal cutting edge of plasma kallikrein cleavage site, a strong staining images were detected around perisinusoidal portions (the right middle case panel in FIG. 9). With the preimmune antibody, no specific staining image was obtained (the right lower case panel in FIG. 9). These results show that active TGF-β and an LAP fragments generated were recognized by each antibody, as a result of a plasma kallikrein-dependent TGF-β activation reaction, which had occurred in the LPS preadministered and partially hepatectomized group. That is to say, such results show that the occurrence of plasma kallikrein-dependent TGF-β activation reaction in the LPS preadministered and partially hepatectomized group is verified using the antibody recognizing N-terminal cutting edge of plasma kallikrein cleavage site. Thus, it revealed the usefulness of the above antibody in animal models.

Example 10

Confirmation of Usefulness in Pathologic Liver in Patient 1

A liver tissue section collected from a patient who died due to fulminant hepatitis was stained with the antibody recognizing N-terminal cutting edge of plasma kallikrein cleavage site (FIG. 10). Thus, the present inventors have succeeded in indicating that a proteolytic TGF-β activation reaction takes place during pathogenesis of human disease.

A section (2.5 μm) was prepared from the human patient liver tissues, which had been fixed with 10% formalin buffer and had been then embedded in paraffin. The section was treated with xylene for 20 minutes 4 times, so as to remove the paraffin. Thereafter, the section was rinsed with ethanol twice, and then with each 90%, 80%, and 70% ethanol once. Thereafter, the section was washed with water and then subjected to air drying. Thereafter, a circle was drawn with a DAKO Pen (DAKO Cytomation, Kyoto, Japan) around the section, and it was further subjected to air drying for 30 minutes. Thereafter, the section was allowed to react with a primary antibody (preimmune antibody (the left panel in FIG. 10)) or the antibody recognizing N-terminal cutting edge of plasma kallikrein cleavage site (the right panel in FIG. 10) at a final concentration of 13 μg/ml, at room temperature for 1 hour in a humanized chamber. After washing with PBS once, the section was further washed for 30 minutes. Thereafter, the section was allowed to react with a 10 µg/ml secondary antibody (Biotin-labeled Swine anti-Rabbit IgG F (ab') 2 fragment (DAKO Cytomation, Kyoto, Japan)) at room temperature for 1 hour. After rinsing with PBS once, the section was further washed for 30 minutes. Thereafter, the section was reacted with alkaline-phosphatase-labeled Strept ABC Complex (DAKO Cytomation, Kyoto, Japan) at room temperature for 40 minutes. After rinsing with PBS once, the section was further washed for 30 minutes. Thereafter, the section was reacted with New Fuchsin substrate (DAKO Cytomation, Kyoto, Japan), which had been prepared according to the instruction included therein, so as to develop color until the background staining was lightly developed in a negative control (the left panel in FIG. 10). The section was lightly rinsed with water, followed by air drying. Thereafter, the section was immersed in xylene for 10 minutes 3 times. The section was mounted on a slide glass with a water-insoluble encapsulating agent, and subjected to microscopic observation.

When compared with the preimmune antibody (the left panel in FIG. 10), hepatic parenchymal cells, which were surrounded around fibers, barely maintained cell structure, were lightly stained with the antibody recognizing N-terminal cutting-edge of plasma kallikrein cleavage site (the right panel in FIG. 10). It was also observed that several cells, recognized as hepatic stellate cells, were stained to red (arrow). These results show that a plasma kallikrein-dependent TGF-β activation reaction takes place during pathogenesis of a patient. Thus, the results strongly suggest a possibility that a specific inhibitor or antibody against plasma kallikrein will be effective against liver failure under fulminant hepatitis.

Example 11

Confirmation of Usefulness in Pathologic Liver in Patient 2

A liver tissue section collected from a patient who died due to hepatitis B was stained. As a result, a clearer stained image could be obtained in the case of using the antibody recognizing N-terminal cutting edge of plasma kallikrein cleavage site than in the case of using the antibody recognizing C-terminal cutting edge of plasma kallikrein cleavage site (FIG. 11).

Liver tissues collected from a patient who died due to hepatitis B were fixed with 10% buffered formalin and then embedded in paraffin, so as to prepare a section (2.5 µm). The section was treated with xylene for 20 minutes 4 times, so as to remove the paraffin, Thereafter, the section was rinsed with ethanol twice, and then with each of 90%, 80%, and 70% ethanol once. Thereafter, it was washed with water and then subjected to air drying. Thereafter, a circle was drawn with a DAKO Pen (DAKO Cytomation, Kyoto, Japan) around the section, and it was further subjected to air drying for 30 minutes, Thereafter, the section was allowed to react with any one of: the antibody recognizing C-terminal cutting edge of plasma kallikrein cleavage site as a primary antibody (which is an antibody recognizing arginine at position 58) (the upper left panel in FIG. 11); the antibody recognizing N-terminal cutting edge of plasma kallikrein cleavage site (which is an antibody recognizing leucine at position 59) (the upper middle panel in FIG. 11); a non-immunized rabbit antibody, all at a final concentration of 13 µg/ml; activated TGF-β-recognizing mouse monoclonal antibody (the upper right panel in FIG. 11); and a non-immunized mouse antibody, both at a final concentration of 1 µg/m, at room temperature for 1 hour in a wet chamber. After rinsing with PBS once, the section was further washed for 30 minutes. Thereafter, the section was reacted with a 10 µg/ml secondary antibody (Biotin-labeled Swine anti-Rabbit IgG F (ab') 2 fragment (DAKO Cytomation, Kyoto, Japan)) or Biotin-labeled Swine anti-Mouse IgG F (ab') 2 fragment (DAKO Cytomation, Kyoto, Japan)) at room temperature for 1 hour. After rinsing with PBS once, the section was further washed for 30 minutes. Thereafter, the section was allowed to react with Horseradish Peroxidase-labeled Strept ABC Complex (DAKO Cytomation, Kyoto, Japan) at room temperature for 40 minutes. After rinsing with PBS once, the section was further washed for 30 minutes. Thereafter, the section was reacted with DAB substrate (DAKO Cytomation, Kyoto, Japan), which had been prepared according to the instruction included therein, so as to develop color until the background was lightly stained in a negative control (the lower case panel in FIG. 11). The section was lightly rinsed with water, followed by air drying. Thereafter, it was penetrated with xylene for 10 minutes 3 times. The section was mounted on a slide glass with a water-insoluble encapsulating agent, and it was subjected to microscopic observation.

When compared with the case of the preimmune antibody (the lower case panel), the cells, mainly, hepatic stellate cells were stained with the antibody recognizing C-terminal cutting edge of plasma kallikrein cleavage site (the upper middle view in FIG. 11). However, a clearer stained image could be obtained in the case of using the antibody recognizing N-terminal cutting edge of plasma kallikrein cleavage site (the upper left view in FIG. 11) than in the case of using the antibody recognizing C-terminal cutting edge of plasma kallikrein cleavage site (the upper middle view in FIG. 11). In the case of the active TGF-β-recognizing mouse monoclonal antibody (the upper right view in FIG. 11) also, the similar staining images as those in the case of using the antibody recognizing C-terminal cutting edge of plasma kallikrein cleavage site (the upper middle view in FIG. 11), but the background thereof was slightly higher (the lower right view in FIG. 11). These results clearly show that a plasma kallikrein-dependent TGF-β activation reaction takes place during pathogenesis in patients. Thus, the results strongly suggest a possibility that a specific inhibitor or antibody against plasma kallikrein will be effective against liver failure occurring under hepatitis B.

Example 12

Confirmation of the Fact that Specific Cleavage of LAP Does Not Takes Place by MMP2 or MMP9

Eight hundred ng of human recombinant LAP β1 (R&D) was incubated at 37° C. for 30 minutes at 27 µl (total amount) of 50 mM Tris buffer (50 mM Tris-HCl (pH 7)-200 mM NaCl-1 µM $ZnCl_2$-5 mM $CaCl_2$-0.05% Brij 35-0.05% $NaN_3$), together with human matrix metalloprotease 2 (MMP2) (Alexis) with a final concentration of 13.3 µg/ml, or with human matrix metalloprotease 9 (MMP9) (Alexis) with a final concentration of 13.3 µg/ml. Thereafter, the resultant was separated through 12.5% polyacrylamide gel electrophoresis, followed by staining with a silver staining knit of Wako Pure Industries, Ltd. However, degradation of LAP could not be confirmed. MMP2 and MMP9 used herein which were purchased were of latent type. Such MMP2 and MMP9 had been incubated with 4-aminophenymercuric acetate (APMA) at a final concentration of 2 mM at 37° C. for 1 hour in the aforementioned 50 mM Tris buffer, so as to activate them. Thereafter, MMP2 and MMP9 were subjected to the experiment. The fact that MMP2 and MMP9 had been activated by the APMA treatment was confirmed by activity measurement of the proteolytic activities using the fluorescent synthetic substance MOCAc-Pro-Leu-Gly-Leu-A2pr (Dnp)-Ala-Arg-NH2 (SEQ ID NO: 5) (manufactured by Peptide Institute, Inc.), performed in 150 mM Tris buffer (150 mM Tris-HCl (pH 7.5)-100 mM NaCl-10 mM CaCl$_2$-0.05% Brij 35) (Ex 280 nm-Em 360 nm; Reference: C. G. Knight, et al., *FEBS Lett.*, volume 296: 263, 1992).

Example 13

Detection of Fragmented LAP by Sandwich ELISA

The sandwich ELISA method was carried out according to certain information (Harlow and Lane, Immunoassays, In Antibodies-A Laboratory Manual, Cold Spring Harbour Laboratory, New York, pp. 553-612, 1988). Namely, 1 µg (50 µl of 20 µg/ml of PBS) of a commercially available anti-human LAP monoclonal antibody (manufactured by R & D) was added per well of an immunoplate (manufactured by Nunc). Thereafter, incubation was carried out at 4° C. overnight for coating. The resultant was washed with PBS twice, and it was then incubated again at 4° C. overnight with 200 µl of a blocking solution (PBS that contained 3% bovine serum albumin-0.02% sodium azide), so as to conduct blocking. The resultant was washed with PBS twice. Thereafter, 50 µl each of dilution series of commercially available human LAP β1 in blocking solution (0, 125, 250, 500, 1,000, and 2,000 ng) (manufactured by R & D), human plasma kallikrein (manufactured by Sigma)-treated (incubation at 37° C. for 40 minutes) human LAP β1 (manufactured by R & D) in blocking solution, or plasmin (manufactured by Sigma)-treated (incubation at 37° C. for 40 minutes) human LAP β1 (manufactured by R & D) in blocking solution was added to each well, followed by reaction at 37° C. for 2 hours. The resultant was washed with PBS 4 times, and thereafter, 40 µl each of PBS solution containing 25 µg/ml the antibody recognizing C-terminal cutting edge of plasma kallikrein cleavage site or pre-immune antibody was added to each well, and the plate was then shaken at room temperature for 2 hours, so as to react it. Thereafter, the reaction product was washed with PBS 4 times, and 100 µl each of an alkaline phosphatase-labeled goat anti-rabbit antibody (manufactured by Jackson; diluted with 7,500-fold PBS-0.05% Tween 20) was added to each well, followed by incubation at 37° C. for 2 hours. The resultant was washed with PBS-0.05% Tween 20 three times, and 200 µl each of a 1 mg/ml p-nitrophenyl phosphate-containing diethanolamine buffer was added thereto. Thereafter, the mixture was incubated at 37° C. for 1 hour. Thereafter, the level of yellow coloration was determined by measuring the absorbance at 405 nm. As a result, it was confirmed that fragmented LAP can be detected (FIG. 12).

INDUSTRIAL APPLICABILITY

In the present invention, a specific antibodies which recognize various protease cleavage sites located in the TGF-β activation controlling region are produced, and these antibodies may detect a pathogenesis-, tissue-, or isoform-specific TGF-β generation reaction (activation reaction). It has been difficult using the prior art techniques to perform such detection. Moreover, using a synthetic low-molecular-weight inhibitor or an antibody specifically inhibiting the thus detected various activation reactions, only abnormal TGF-β generation reactions can be suppressed. Thus, it is anticipated that the present invention be useful for the diagnosis of a novel method for treatment method or the diagnosis of prognosis.

---

The invention claimed is:

1. A method for detecting or measuring the activation reactions of human TGF-β1, human TGF-β2, and/or human TGF-β3 existing in samples or tissues comprising:

staining or reacting a sample or tissue with an antibody against a latency-associated peptide (LAP) fragment of human TGF-β, which is able to specifically recognize a protease cleavage site within human TGF-β.

2. A method for diagnosing sclerotic diseases comprising:

detecting or measuring the activation reactions of human TGF-β1, human TGF-β2, and/or human TGF-β3 existing in samples or tissues using an antibody against an LAP fragment of human TGF-β, which is able to specifically recognize a protease cleavage site within human TGF-β; and diagnosing sclerotic diseases based on the detection or measurement.

3. A method for detecting or measuring the activation reactions of human TGF-β1, human TGF-β2, and/or human TGF-β3 existing in samples or tissues comprising:

staining or reacting a sample or tissue with using an antibody against an LAP fragment of human TGF-β1, human TGF-β2 and/or human TGF-β3, which is able to specifically recognize respective cutting edges within protease cleavage sites existing in the region from the amino acid residue glycine at position 51 to the amino acid residue arginine at position 110 of SEQ ID NO: 1, and corresponding regions of human TGF-β2 and human TGF-β3.

4. The method of claim 1, wherein the antibody is a polyclonal antibody.

5. The method of claim 1, wherein the antibody is a monoclonal antibody.

6. The method of claim 1, wherein the antibody specifically recognizes the cutting edge ending at the leucine residue at position 59, and a protease cleavage site is between the arginine residue at position 58 and the leucine residue at position 59.

7. The method of claim 1, wherein the antibody specifically recognizes the cutting edge ending at the arginine residue at position 58, and a protease cleavage site is between the arginine residue at position 58 and the leucine residue at position 59.

8. The method of claim 1, wherein the antibody specifically recognizes the cutting edge ending at the leucine residue at position 57, and a protease cleavage site is between the lysine residue at position 56 and the leucine residue at position 57.

9. The method of claim 1, wherein the antibody specifically recognizes the cutting edge ending at the lysine residue at position 56, and a protease cleavage site is between the lysine residue at position 56 and the leucine residue at position 57.

10. The method of claim 1, wherein the antibody specifically recognizes the cutting edge ending at the leucine residue at position 80, and a protease cleavage site is between the alanine residue at position 79 and the leucine residue at position 80.

11. The method of claim 1, wherein the antibody specifically recognizes the cutting edge ending at the alanine residue at position 79, and a protease cleavage site is between the alanine residue at position 79 and the leucine residue at position 80.

12. The method of claim 1, wherein the antibody specifically recognizes the cutting edge ending at the aspartic acid residue at position 86, and a protease cleavage site is between the arginine residue at position 85 and the aspartic acid residue at position 86.

13. The method of claim 1, wherein the antibody specifically recognizes the cutting edge ending at the arginine residue at position 85, and a protease cleavage site is between the arginine residue at position 85 and the aspartic acid residue at position 86.

14. The method of claim 1, wherein the antibody specifically recognizes the cutting edge ending at the glutamic acid residue at position 107, and a protease cleavage site is between the lysine residue at position 106 and the glutamic acid residue at position 107.

15. The method of claim 1, wherein the antibody specifically recognizes the cutting edge ending at the lysine residue at position 106, and a protease cleavage site is between the lysine residue at position 106 and the glutamic acid residue at position 107.

16. The method of claim 1, wherein the antibody specifically recognizes the cutting edge ending at the valine residue at position 77, and a protease cleavage site is between the alanine residue at position 76 and the valine residue at position 77.

17. The method of claim 1, wherein the antibody specifically recognizes the cutting edge ending at the alanine residue at position 76, and a protease cleavage site is between the alanine residue at position 76 and the valine residue at position 77.

18. The method of claim 2, wherein the sclerotic disease is hepatic fibrosis/cirrhosis, atherosclerosis, lung fibrosis, scleroderma, or renal failure.

* * * * *

UNITED STATES PATENT AND TRADEMARK OFFICE
CERTIFICATE OF CORRECTION

| | | |
|---|---|---|
| PATENT NO. | : 7,803,553 B2 | Page 1 of 1 |
| APPLICATION NO. | : 10/570606 | |
| DATED | : September 28, 2010 | |
| INVENTOR(S) | : S. Kojima et al. | |

It is certified that error appears in the above-identified patent and that said Letters Patent is hereby corrected as shown below:

On the Title page under Item [57] Abstract, line 6 of the printed patent, "TGOF-β2" should be --TGF-β2--.

Signed and Sealed this
Twenty-sixth Day of April, 2011

David J. Kappos
*Director of the United States Patent and Trademark Office*